(12) United States Patent
Das et al.

(10) Patent No.: US 10,352,847 B2
(45) Date of Patent: Jul. 16, 2019

(54) MOBILE DEVICE BASED FLUID TESTING APPARATUS

(71) Applicant: Labby Inc., Brighton, MA (US)

(72) Inventors: Anshuman Jyothi Das, Brighton, MA (US); Akshat Wahi, Kidwai Nagar (IN)

(73) Assignee: LABBY INC., Brighton, MA (US)

( * ) Notice: Subject to any disclaimer, the term of this patent is extended or adjusted under 35 U.S.C. 154(b) by 0 days.

(21) Appl. No.: 16/017,997

(22) Filed: Jun. 25, 2018

(65) Prior Publication Data
US 2018/0372623 A1 Dec. 27, 2018

Related U.S. Application Data

(60) Provisional application No. 62/525,102, filed on Jun. 26, 2017.

(51) Int. Cl.
| | |
|---|---|
| *G01J 3/28* | (2006.01) |
| *G01N 21/31* | (2006.01) |
| *G01N 33/14* | (2006.01) |
| *G01N 21/03* | (2006.01) |
| *G01J 3/00* | (2006.01) |
| *G01N 15/00* | (2006.01) |
| *G01N 21/80* | (2006.01) |
| *G01N 21/84* | (2006.01) |
| *G01N 21/51* | (2006.01) |
| *G01N 21/64* | (2006.01) |
| *G01N 21/85* | (2006.01) |
| *G01N 21/01* | (2006.01) |

(52) U.S. Cl.
CPC .............. *G01N 21/31* (2013.01); *G01J 3/00* (2013.01); *G01N 15/00* (2013.01); *G01N 21/03* (2013.01); *G01N 21/80* (2013.01); *G01N 21/8483* (2013.01); *G01N 33/146* (2013.01); *G01N 21/51* (2013.01); *G01N 21/645* (2013.01); *G01N 21/85* (2013.01); *G01N 2021/0118* (2013.01); *G01N 2021/0346* (2013.01); *G01N 2201/0221* (2013.01)

(58) Field of Classification Search
CPC .... G01J 3/02; G01J 3/28; G01J 3/2803; G01J 3/10; G01J 3/2823
USPC ........................................................ 356/326
See application file for complete search history.

(56) References Cited

U.S. PATENT DOCUMENTS

| | | | |
|---|---|---|---|
| 6,535,753 B1* | 3/2003 | Raskas | A61B 5/14514 600/310 |
| 2005/0107676 A1* | 5/2005 | Acosta | A61B 5/14532 600/316 |
| 2013/0089876 A1* | 4/2013 | Sadik | G01N 21/6428 435/7.92 |

\* cited by examiner

*Primary Examiner* — Md M Rahman
(74) *Attorney, Agent, or Firm* — Foley & Lardner LLP; James De Vellis

(57) ABSTRACT

The present disclosure describes devices and techniques for testing. In particular, the disclosure describes testing systems that are portable and easy to operate. The testing system can include a measurement apparatus that can be used to measure spectral characteristics of a sample and can be in a portable, hand-held form-factor. The testing system also includes a computing device, such as a mobile phone, a laptop, or a personal computer that can communicate with the measurement device over a wired or a wireless communication link and also can have form-factors that are portable. The computing device can run applications or programs that receive spectral data of the sample from the measurement apparatus and can process the received spectral data to determine various properties of the sample. As both the measurement apparatus and the computing device are portable, the measurements can be easily made at site where the fluid is produced.

20 Claims, 29 Drawing Sheets

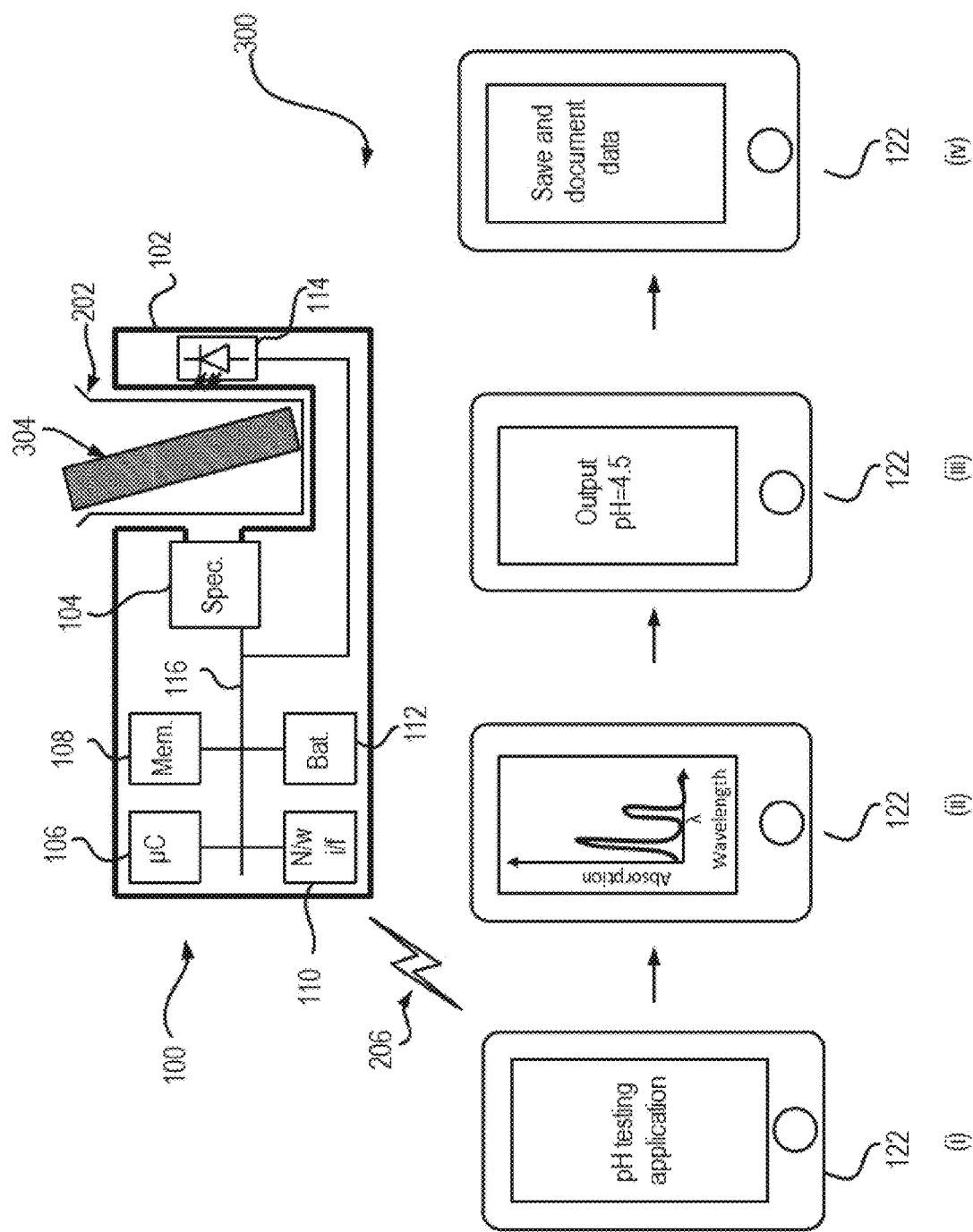

MOBILE DEVICE BASED FLUID TESTING APPARATUS

RELATED APPLICATION

The present application claims priority under 35 U.S.C. § 119 to U.S. Provisional Patent Application 62/525,102, filed Jun. 26, 2017 and titled "MOBILE DEVICE BASED BEVERAGE AND BEVERAGE MANUFACTURING PROCESS TESTING," which is incorporated herein by reference in its entirety.

BACKGROUND

Fluids such as beverages, when produced in batches from their component ingredients can vary from batch to batch in color, composition, or other characteristics. This lack of uniformity or repeatability can cause variances in the finished product. Testing of fluids or their component ingredients may require dedicated laboratories that are remote from the place of manufacture of the fluids or from the source of the ingredients.

SUMMARY

One aspect of this disclosure is directed to a system for testing fluid samples. The system can include a portable testing apparatus. The portable testing apparatus can include a head portion having a length of between 2 centimeters and 3 centimeters, a width of between 3 centimeters and 4 centimeters, and a height of between 2 centimeters and 4 centimeters. The head portion can include a sample aperture to receive a fluid sample and a light source to direct light towards the fluid sample. The portable device can include a body portion coupled to the head portion. The body portion can have a length of between 5 centimeters and 10 centimeters, a width of between 4 centimeters and 7 centimeters, and a height equal to the height of the head portion. The body portion can include a microcontroller, a memory, a battery, a network interface, and a spectrometer. The spectrometer can be aligned with the light source of the head portion to receive the light from the light source after the light has passed through the fluid sample to produce spectral data. The system can also include a computing device communicatively coupled to the portable testing apparatus via the network interface of the portable testing apparatus to receive the spectral data from the portable testing apparatus. The computing device can include an electronic processor that executes an application to process the spectral data to generate a measurement value of the fluid sample.

Another aspect of this disclosure is directed to a method of testing fluid samples. The method can include receiving, in a sample aperture of a head portion of a portable testing apparatus, a fluid sample. The head portion can have a length of between 2 centimeters and 3 centimeters, a width of between 3 centimeters and 4 centimeters, and a height of between 2 centimeters and 4 centimeters. The method can include activating a light source included in the head portion of the portable testing apparatus to direct light toward the fluid sample. The method can include receiving, by a spectrometer included in a body portion of the portable testing apparatus, the light from the light source after the light has passed through the fluid sample. The method can include producing, by the spectrometer, spectral data based on the light received from the light source. The method can include transmitting, via network interface included in the body portion of the portable testing apparatus, the spectral data to a computing device. The method can include executing, by the computing device, an application to process the spectral data to generate a measurement value of the fluid sample.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

FIG. 3A shows a testing system for measurement of a pH level of a pH strip using the testing apparatus shown in FIG. 1.

Figure 1:
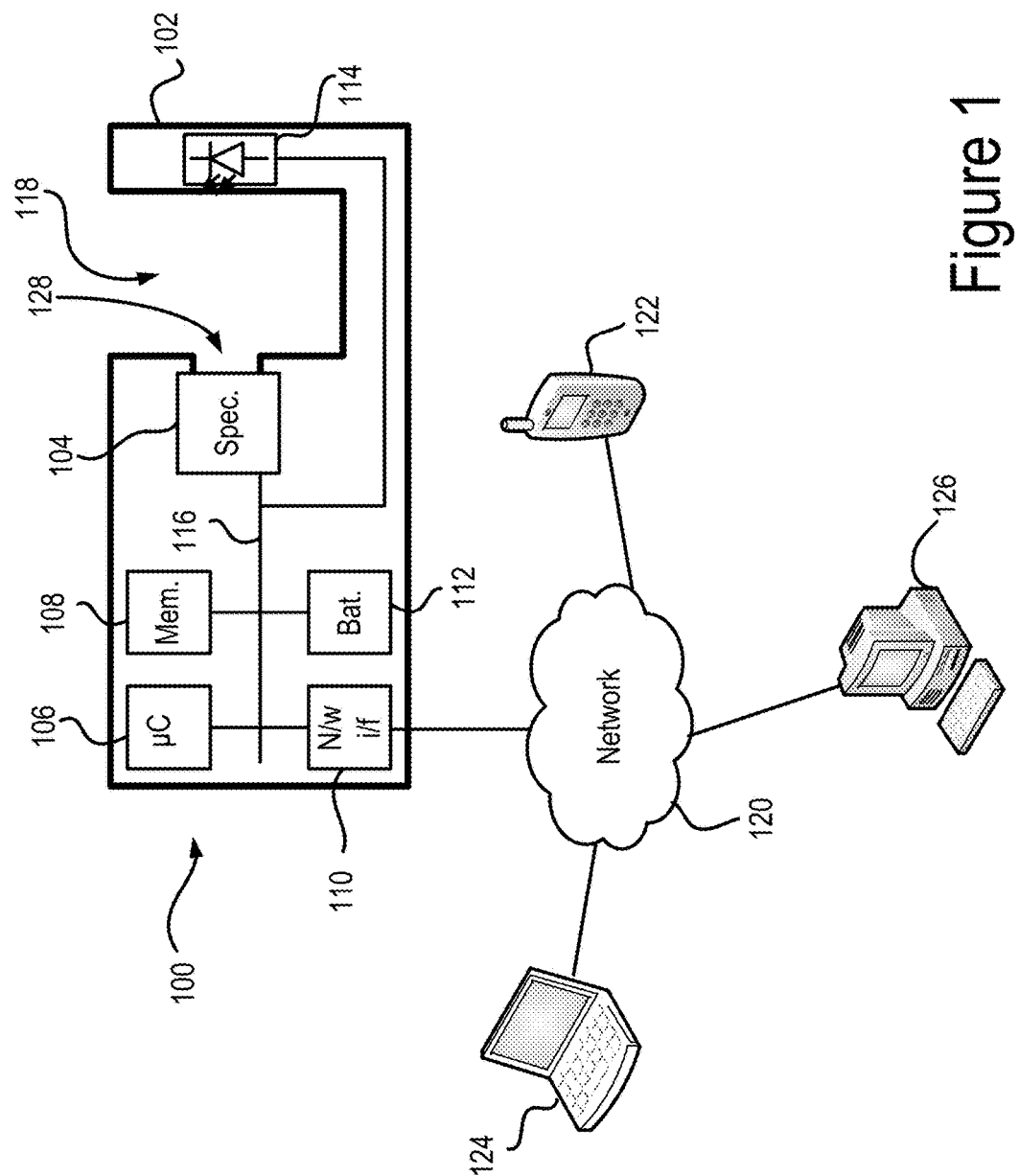
FIG. 1 illustrates a representation of an example testing apparatus.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

DETAILED DESCRIPTION

The present disclosure describes devices and techniques for testing the quality of fluids such as beverages (or of their component ingredients) such as beer, wine, or milk. In particular, the disclosure describes testing systems that are portable and easy to operate. The testing system can include a testing or measurement apparatus that can be used to measure spectral characteristics of a sample. The testing apparatus can be in a hand-held form-factor and can be portable, which allows the measurement apparatus to be used on the field where the sample is grown or manufactured. The testing system can also include a computing device, such as a mobile phone, smartphone, tablet, laptop, personal computer, or server (local or remote) that can communicate with the measurement device over a direct, wired or a wireless communication link. The mobile phone or the laptop also can have form-factors that are portable. The computing device can run applications or programs that receive spectral data of the sample from the measurement apparatus. The applications or program can process the received spectral data and determine various properties of the sample. The measurement apparatus and the computing device can work together to perform all of the operations discussed herein. The measurement apparatus and the computing device can be portable handheld units, so that the measurements can be made and results obtained onsite where the beer or wine is made or where the grape is grown, e.g., in a brewery, factory, or a vineyard. Further, the ease of use of the application can allow non-specialist users to use the testing system.

FIG. 1 illustrates a representation of an example testing apparatus 100. The testing apparatus 100 can include at least one device enclosure 102, at least one spectrometer 104, at least one microcontroller 106, at least one memory 108, at least one network interface 110, at least one battery 112 (or other power source), at least one light source 114, and at least one communication bus 116. The device enclosure 102 can include at least one sample slot 118, in which a container containing a beverage under test can be placed. The testing apparatus 100 can connect to at least one network 120, which, in turn, can be connected to one or more computing devices, such as at least one mobile device 122, at least one laptop 124, or at least one personal computer or server 126.

The light source 114 can include at least one light emitting diode (LED), at least one filament bulb, at least one fluorescent light source, or other light source. The light source 114 can provide light having various wavelengths. For example, the light source 114 can provide white light, blue light, green light, red light, or a combination thereof. The wavelength(s) of light emitted by the light source 114 can be selected by the microcontroller 106. The spectrometer 104 can be positioned opposite from the light source 114 such that at least a portion of the light emitted by the light source 114 can pass through a beverage sample and be incident on the spectrometer 104. To that end, the device enclosure 102 can include an opening 128 that allows light to be incident on the spectrometer 104. The spectrometer 104 can measure the spectral characteristics of the incident light. For example, the spectrometer 104 can measure the intensity of one or more wavelengths or one or more wavelength ranges.

The microcontroller 106 can control the operation of the testing apparatus 100. For example, the microcontroller can be configured to execute one or more programs or software applications stored in the memory 108. The microcontroller 106 can also control the operation of the spectrometer 104, the light source 114, the memory 104, the network interface 110, and the battery 112. The microcontroller 106 can receive measurement data from the spectrometer 104 and can store the received measurement data in memory 108 and transmit the received measurement data via the network interface. The memory 108 can include volatile and non-volatile memory. For example, the memory 108 can include a RAM, ROM, flash memory, hard-drive, optical drive, or other memory devices. The network interface 110 can provide communication over the network 120. The network interface 110 can provide wired or wireless communication. For example, the network interface 110 can include a network interface card to connect to wired networks such as Ethernet, LAN, WAN, and other wired networks. The network interface 110 also can include wireless interface cards for connecting to wireless networks such as WiFi Ethernet, Bluetooth, ZigBee, cellular networks (e.g., 3G, 4G, LTE, etc.) or other wireless networks. The network interface 110 also can provide communications using parallel or serial communication protocols such as USB, FireWire, and other peripheral connection so that the testing apparatus can communicate with control software without wireless communications. For example the testing apparatus 100 (or component thereof such as a memory card) can plug into a smartphone or other computing device to access an app or script that can analyze data obtained by the testing apparatus. The battery 112 (or other power source) can be a rechargeable battery, such as a lithium-ion battery, and can be monitored by the microcontroller. The testing apparatus 100 can include analog and digital circuitry for operation of the light source 114, the spectrometer 104, the battery 112, and the network interface 110, the microcontroller 106 and the memory 108. One or more of the components of the testing apparatus can communicate over a communication bus 116.

Figure 2A:
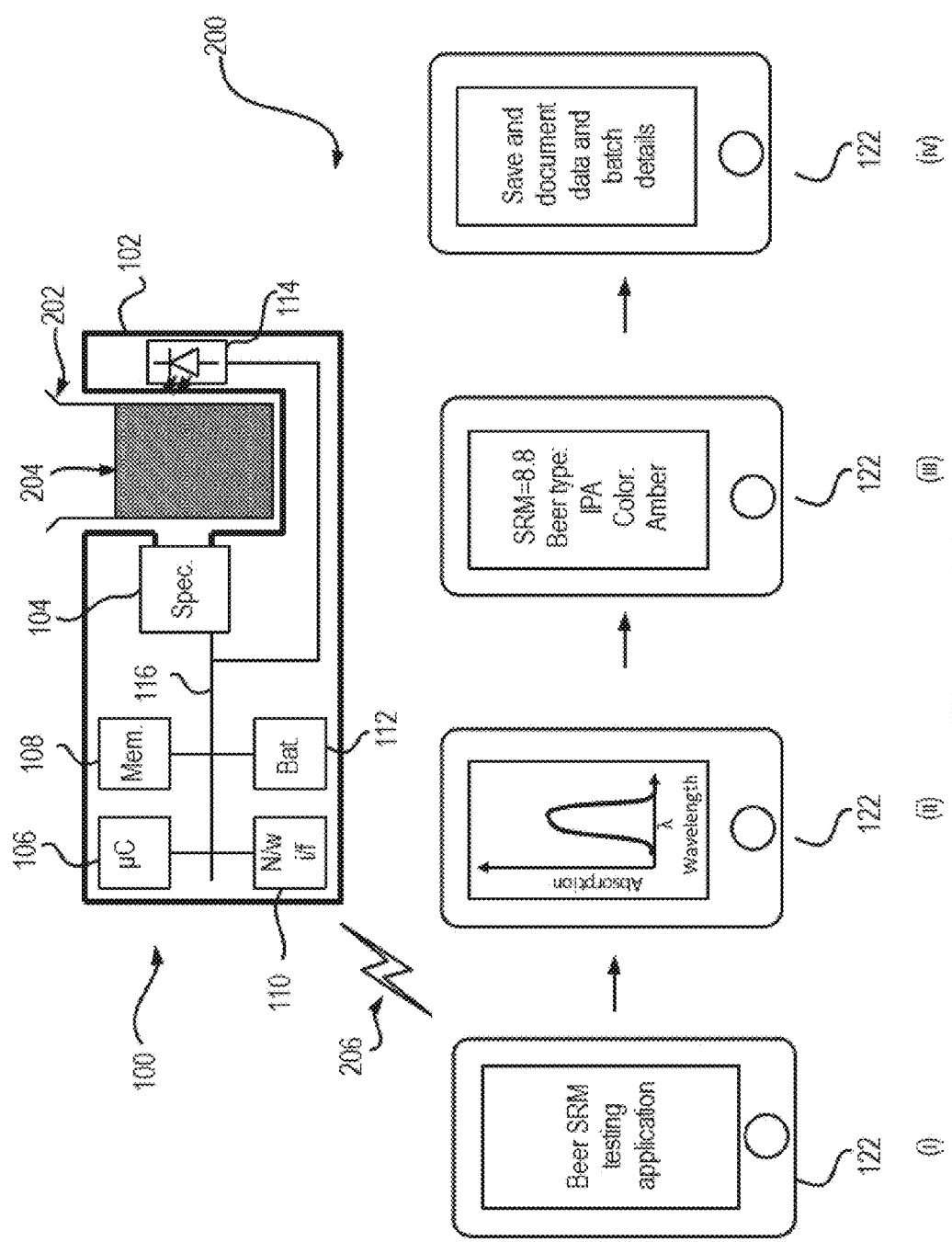
FIG. 2A shows a testing system for measurement of a standard reference method (SRM) number for a beer using the testing apparatus shown in FIG. 1.
Figure 2B:
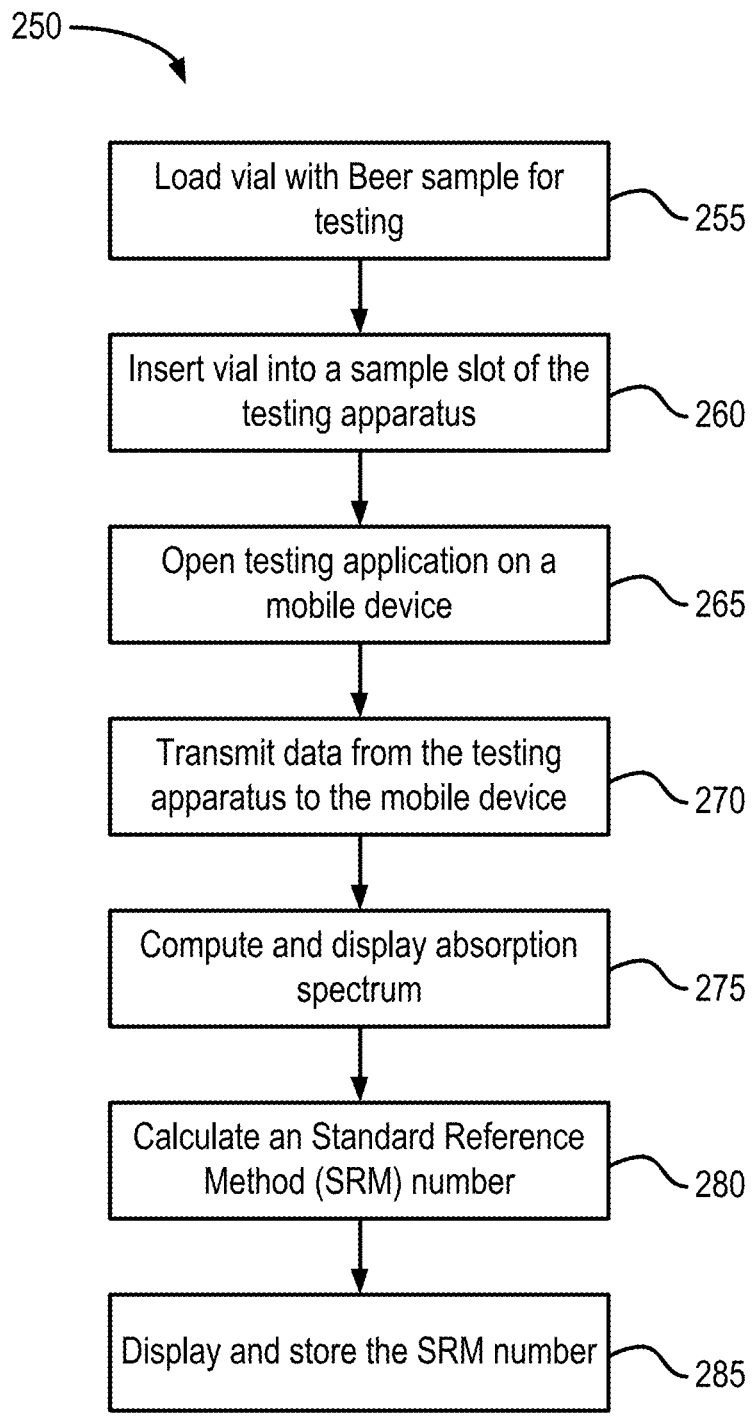
FIG. 2B shows a flow diagram representing an example process for operating the testing system shown in FIG. 2A.

FIG. 2A shows a testing system 200 for measurement of a standard reference method (SRM) number for a beer using the testing apparatus shown in FIG. 1. FIG. 2B shows a flow diagram 250 representing an example process for operating the testing system 200 shown in FIG. 2A. FIG. 2A also shows example representations of status of a mobile device corresponding to one or more stages of the process 250. The SRM number for beer is an industry standard set by the American Society of Brewing Chemists (ASBC) to standardize the color of the beer. In one example implementation, the SRM number can be calculated by assessing the absorption of light at 430 nm (blue) region of the visible spectrum of light. For example, the SRM can be determined using the following equation: SRM=12.7×Abs. at 430 nm×D, where D is a dilution factor. The SRM number can serve as a distinguishing factor for beer samples as it can classify a beer sample into specific color categories e.g. amber, straw, dark etc. It can also be used as a metric for repeatability of a recipe which can be useful feedback for a brewer. The present solution includes remote handheld devices that can measure spectra of the beer sample (or other sample such as wine or grapes) without the need to resort to a remote, fixed location lab environment. For example small breweries may lack the resources to outsource the SRM test to a lab service provider and may instead forego the test due to lack of equipment. The system and technique discussed herein can perform SRM measurement on a smartphone platform at the comfort of any facility or even at home. This can empower homebrewers, craft breweries, and brewpubs to perform in-house or field tests in real time (e.g., same day) without having to send samples to remote third party laboratories.

Referring to FIG. 2B, among others, the process 250 can include receiving, by the testing apparatus, a vial with a beer sample. For example, the process can include loading a vial with a beer sample for testing (stage 255) and inserting the vial into a sample slot of the testing apparatus (stage 260). This is shown in FIG. 2A, where the testing apparatus 100 receives a vial 202 containing a beer sample 204 in the sample slot 118 of the testing apparatus 100. The process 200 further includes receiving an indication from the mobile device that a testing application has been launched (stage 265). This is shown in FIG. 2A(i), where the launching of a beer (or other fluid) SRM testing application is launched on the mobile device 122. After launching the testing application, the testing application can establish a wireless communication 206 (such as a Bluetooth communication) or a wired communication (such as a USB connection) with the testing apparatus 100. The application can instruct the testing apparatus to proceed with the measurement of the sample 204. The process 250 further includes transmitting data from the testing apparatus 100 to the mobile device 122 (stage 270) and computing and displaying absorption spectrum of the sample (stage 275). This is shown in FIG. 2A(ii) where the testing application running on the mobile device processes the measurement data received from the testing apparatus 100 and determines the absorption spectra of the beer sample. The application displays a graphical representation or visualization of the spectra on an electronic display screen of the mobile device 122. The process 250 also includes calculating the SRM of the beer sample (stage 280). In some example implementations, the application can use the SRM formula discussed above to determine the SRM of the beer sample. The process 250 further includes the testing application displaying the resulting SRM on a display screen and storing the SRM as well as batch details in memory (stage 285). This is shown in FIG. 2A(iii) and FIG. 2A(iv), where the application displays on a display screen of the mobile device 122 the calculated SRM (e.g., SRM=8.8). The testing application also can store in memory of the mobile device 122, the SRM data along with the corresponding batch data of the sample beer tested. While the application discussed above is shown to be running on a mobile device, the application can also run on a laptop, a personal digital assistant, an tablet, a laptop, or a personal computer.

Figure 3B:
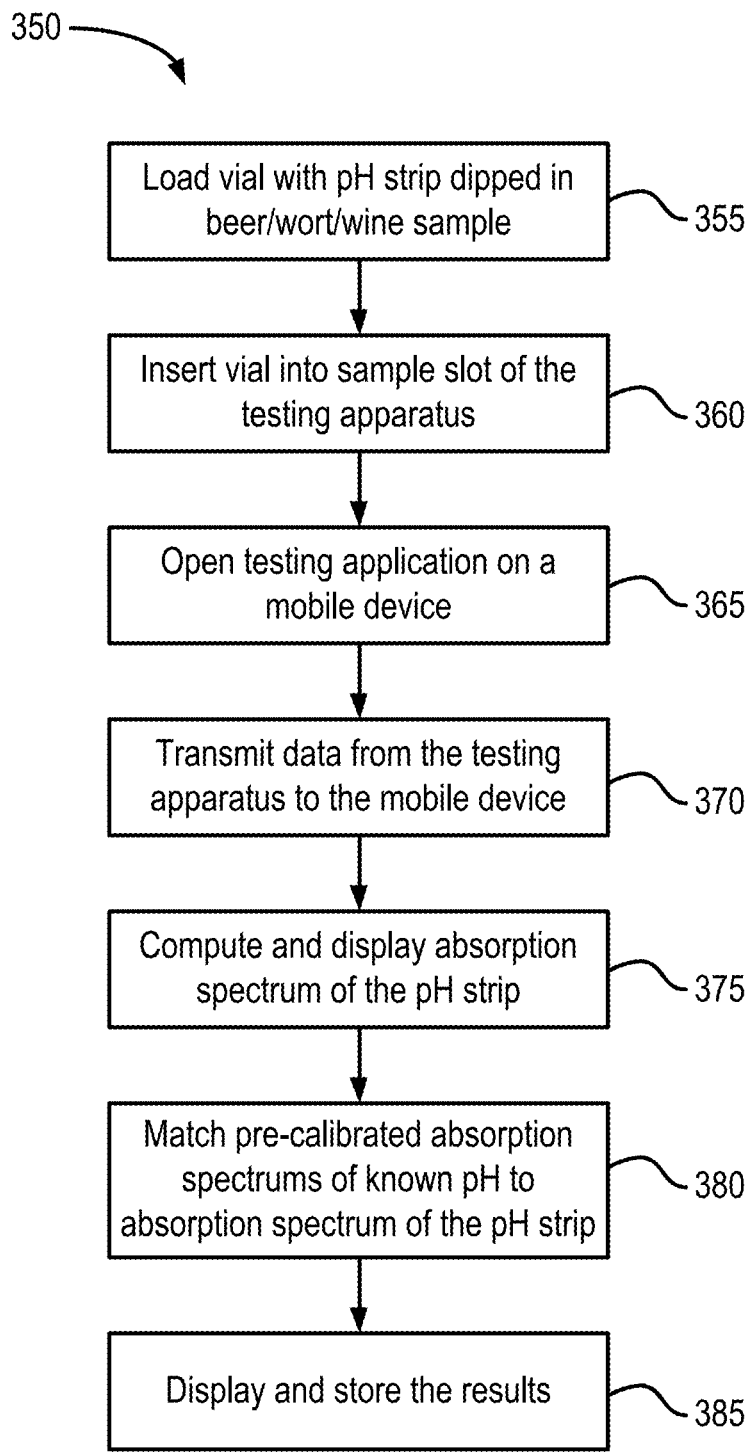
FIG. 3B shows a flow diagram representing an example process for operating the testing system shown in FIG. 3A.

FIG. 3A shows a testing system 300 for measurement of a pH level of a pH strip using the testing apparatus shown in FIG. 1. FIG. 3B shows a flow diagram 350 representing an example process for operating the testing system 300 shown in FIG. 3A. FIG. 3A also shows example representations of status of a mobile device 122 corresponding to one or more stages of the process 350. Measuring pH is an important consideration during the brewing or winemaking process and can decide the final taste of the product, and pH can be tested using a pH strip, which changes color after coming in contact with the beer or wine begin tested, and comparing its color with a printed color guide. This can be erroneous and subjective and can depend on the user's color perception. Another method is to use an electronic pH tester which is accurate but can be expensive. The ability to measure pH repeatedly with good accuracy can lead to better control over the taste of the final product. An optical readout, provided by the system and techniques discussed below, is fast and accurate and performs better than having to match a color guide. The optical readout of pH is provided on a smartphone platform by reading the color of a pH strip accurately and then matching it with the previously obtained pre-calibrated set of pH strips. The unknown color can be easily matched and the readout can be instantaneous at the same time maintain accuracy. This process can be repeated and done frequently during production.

The stages 355, 360, 365, and 370 of the process 350 are similar to the stages 255, 260, 265, and 270 of the process 250 discussed above, except that in the process 350, a pH strip, instead of a fluid beer sample is received by the testing apparatus 100. FIG. 3A shows the testing apparatus receiving, in the sampling slot 118, a pH strip 304 placed in a vial 202. A pH testing application is launched on the mobile device 122, as shown in FIG. 3A(i). The pH testing application can instruct the testing apparatus 100 to proceed with the measurement of the pH strip 304. Data measured by the testing apparatus 100 is transmitted to the mobile device 122 and provided to the pH application. Process 350 includes the application computing and displaying the absorption spectrum of the pH strip (stage 375). This is shown in FIG. 3A(ii), where the pH application displays the absorption spectrum of the pH strip on the display screen of the mobile device 122. The process further includes the pH application matching the color of the pH strip to a closest color in a pre-determined set of colors (stage 380). The set of pre-determined colors can be stored in the mobile device 112, and can include colors of pH strip determined by commercial pH meters. The process 350 also includes the pH application displaying and storing the results in memory (stage 385). This is shown in FIG. 3A(iii) and (iv), where the pH application displays the determined pH level on the display screen of the mobile device 122, and stores the data in memory. While the pH application discussed above is shown to be running on a mobile device 122, the application can also run on a laptop, a personal digital assistant, an tablet, a laptop, or a personal computer.

Figure 4A:
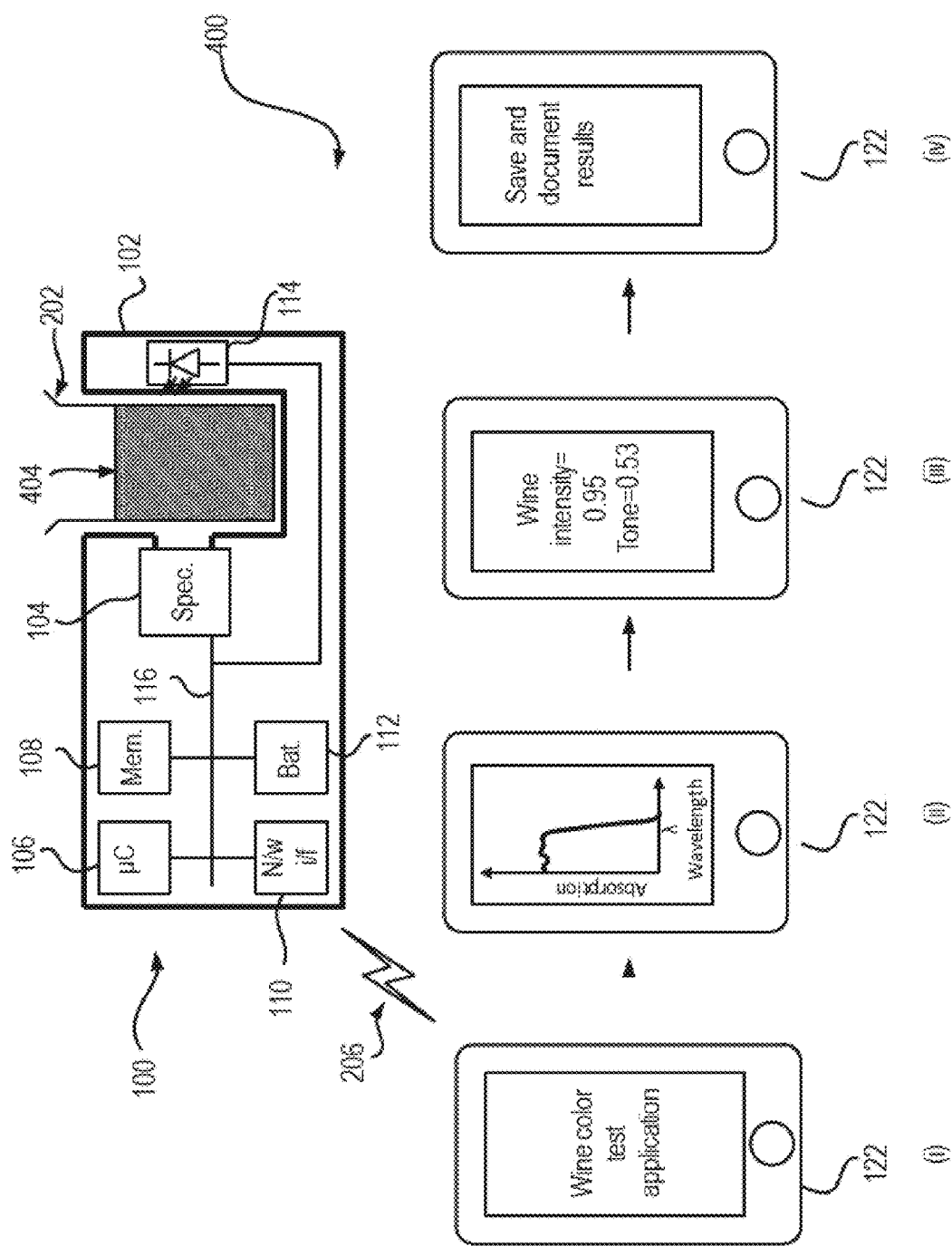
FIG. 4A shows a testing system for measurement of a color and intensity levels of a wine sample using the testing apparatus shown in FIG. 1.
Figure 4B:
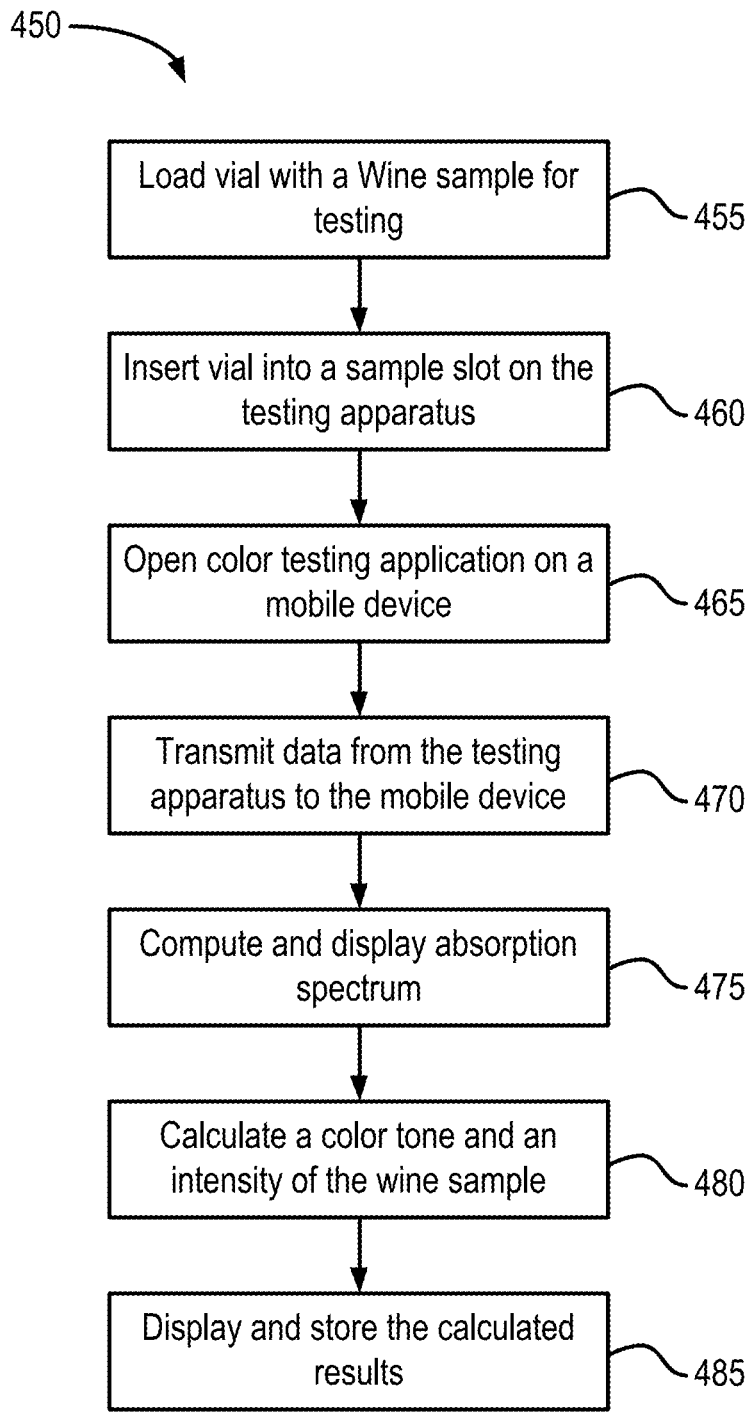
FIG. 4B shows a flow diagram representing an example process for operating the testing system shown in FIG. 4A.

FIG. 4A shows a testing system 400 for measurement of a color and intensity levels of a wine sample 404 using the testing apparatus 100 shown in FIG. 1. FIG. 4B shows a flow diagram 450 representing an example process for operating the testing system 400 shown in FIG. 4A. FIG. 4A also shows example representations of status of a mobile device 122 corresponding to one or more stages of the process 450. The tone and color of wine is an important metric of aging, the type of wine and a quality parameter. For example, when a red wine ages its tone and intensity changes to lower values and it appears pale over time. Generally this is challenging to determine as these changes are subtle and difficult to perceive with the naked eye. The system and techniques discussed below in relation to FIGS. 4A and 4B discuss implementing accurate determination of wine tone and intensity at the comfort of any setting, be it home or production facility on a portable platform. This will enable many users to make this measurement at a fraction of the cost of conventional lab equipment. In one example implementation, the tone and intensity of wine can be calculated using the Sudraud method which evaluates the absorption of light at 420 nm (blue) and 520 nm (green) regions of the visible optical spectrum. For the tone (hue/tint) the ratio of absorption at 420 nm to 520 nm is calculated. For the intensity the sum of absorption at 420 nm and 520 is considered.

Stages 455, 460, 465, 470, and 475 of the process 450 are similar to the corresponding process stages discussed above in relation to processes 350 and 250, and are not discussed in further detail. Stage 480 of the process 400 includes the wine color test application calculating a color tone and intensity of the wine sample. As mentioned above, the color tone and intensity can be calculated for example using the Sudraud method. To calculate the color tone, the wine color test application can determine the absorption levels at 420 nm and 520 nm wavelengths of light, and calculate a ratio of the absorption at 420 nm over the absorption at 520 nm. To determine the intensity, the application can determine the sum of the absorption at 420 nm and that at 520 nm. The process 450 also includes the application displaying the calculated tone and intensity of the wine on a display, and storing the calculated tone and intensity in memory, in stage 485. This is shown in FIG. 4A(iii) and (iv), where the wine color test application displays the calculated tone and intensity values (e.g, intensity=0.95 and tone=0.53) on the display screen of the mobile device 122, and stores the calculated data in memory. While the wine color test application discussed above is shown to be running on a mobile device 122, the application can also run on a laptop, a personal digital assistant, an tablet, a laptop, or a personal computer.

Figure 5A:
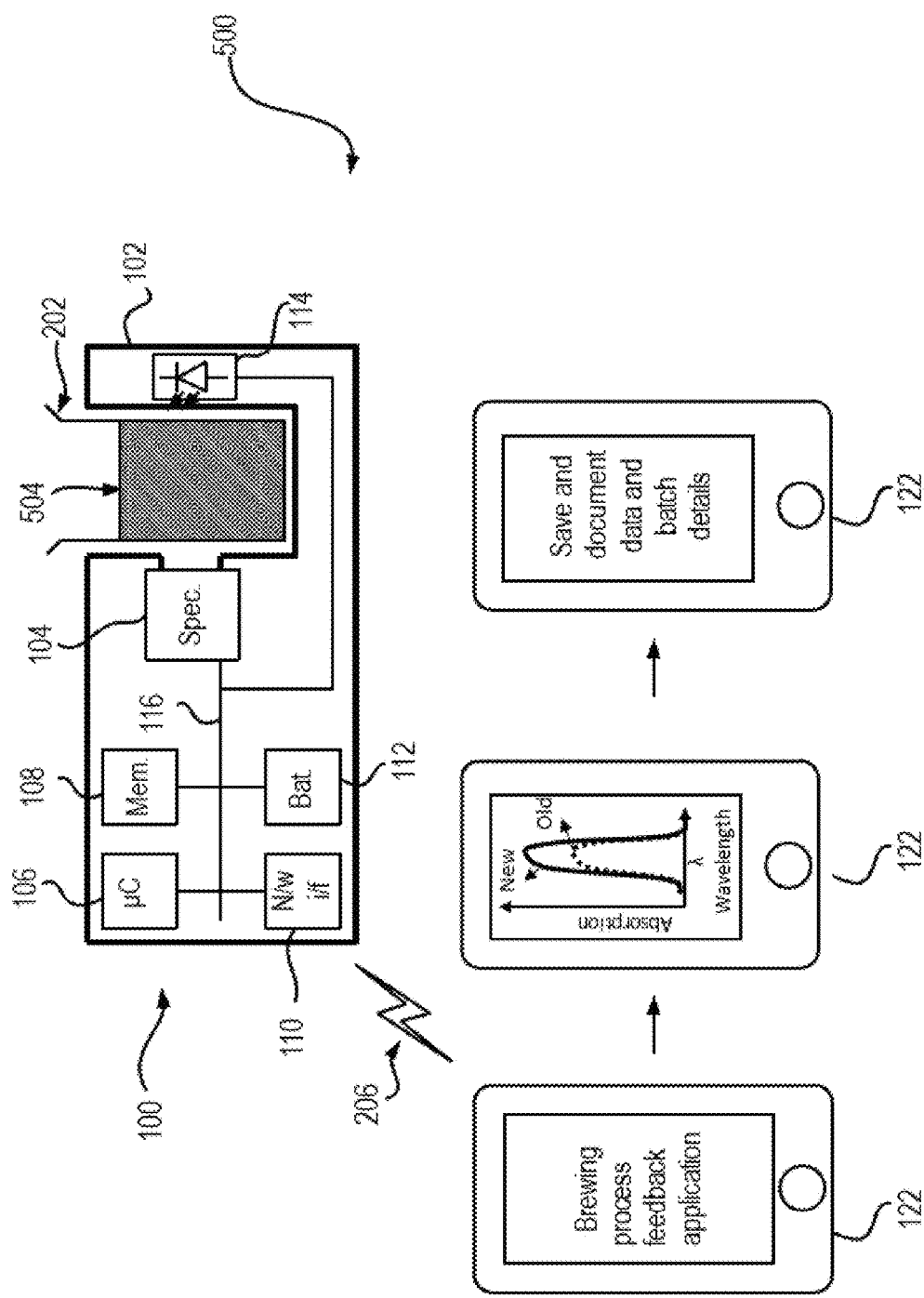
FIG. 5A shows a testing system for beer production testing and monitoring using the testing apparatus shown in FIG. 1.
Figure 5B:
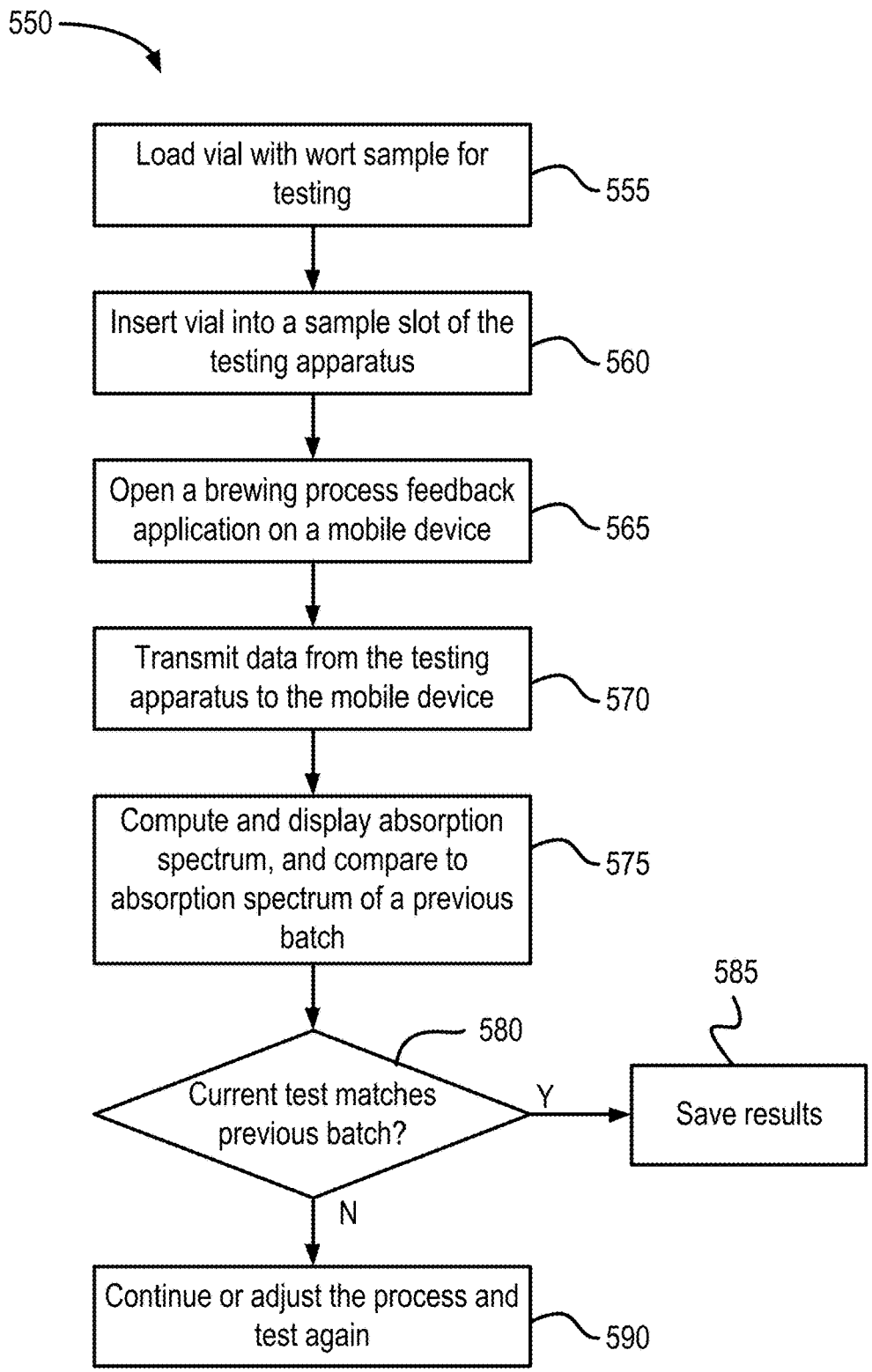
FIG. 5B shows a flow diagram representing an example process for operating the testing system shown in FIG. 5A.

FIG. 5A shows a testing system 500 for beer production testing and monitoring using the testing apparatus shown in FIG. 1. FIG. 5B shows a flow diagram 550 representing an example process for operating the testing system 500 shown in FIG. 5A. FIG. 5A also shows example representations of status of a mobile device 122 corresponding to one or more stages of the process 550. Brewing is carried out in many stages from the initial milling, mashing, lautering, sparging, boiling, fermenting, conditioning, filtering and packaging. Each of this stages witness a color change in the wort or the sugar-rich intermediate that turns into alcohol. Generally, the wort is visually analyzed in terms of color and there are not many objective assessments made during the brewing process. This can lead to dissimilar products even if the initial amount of grains, hops and the overall process was performed in an identical manner. There are temperature fluctuations among other variables that need to be carefully accounted for throughout the brewing process. The system and process discussed below with reference to FIGS. 5A and 5B provide frequent evaluation of the wort color at different stages and provide feedback to the brewer using a portable measuring apparatus connected to a mobile device. This can lead to an optimized process where subsequent steps can be adjusted to match a previously brewed product. This in turn can lead to a consistent product and can mitigate effects of other variables lead to dissimilar batches of products even when the starting point and initial amounts of raw materials was identical. The process 550 is carried out using a wort sample 504, as shown in FIG. 5A.

Stages 555, 560, 565, and 570 of the process 550 are similar to the corresponding process stages in the processes 250, 350, and 450 discussed above, and are not discussed in further detail. At stage 575, the brewing process feedback application computes and displays the absorption spectrum to the user on the display screen, as shown in FIG. 5A(ii). The application also simultaneously displays the absorption spectrum of one or more previous batches of beer. Based on the current and previous spectra, the application, or the user, can determine whether the current batch meets the degree of desired consistency with previous batches (stage 580). If it is determined by the application that the current batch is consistent with the previous batches within a certain degree, then the application can save the results of the spectra of the current batch (stage 585). If however, the application determines that the current batch is not consistent with the previous batches within a certain degree, then the application or the user can determine whether to continue with the brewing process or to start a new batch (stage 590). The testing of the spectrum of the wort can be carried out at various stages of brewing of the beer, such as, for example, during lautering, sparging, rinsing, boiling, carbonating, etc. While the brewing process feedback application discussed above is shown to be running on a mobile device 122, the application can also run on a laptop, a personal digital assistant, an tablet, a laptop, or a personal computer.

Figure 6A:
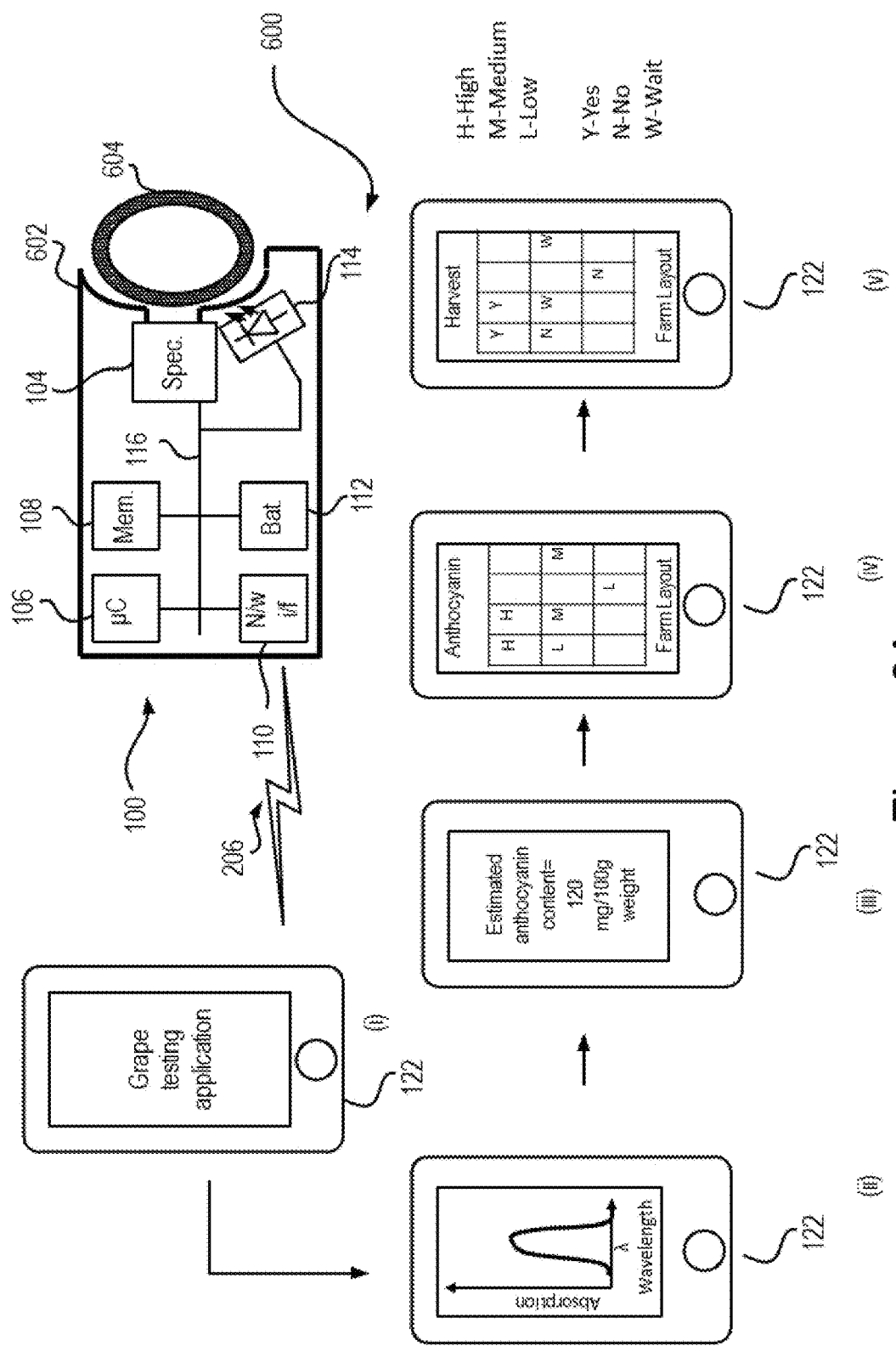
FIG. 6A shows a testing system for measurement of anthocyanin levels in a grape sample using a testing apparatus similar to the one shown in FIG. 1.
Figure 6B:
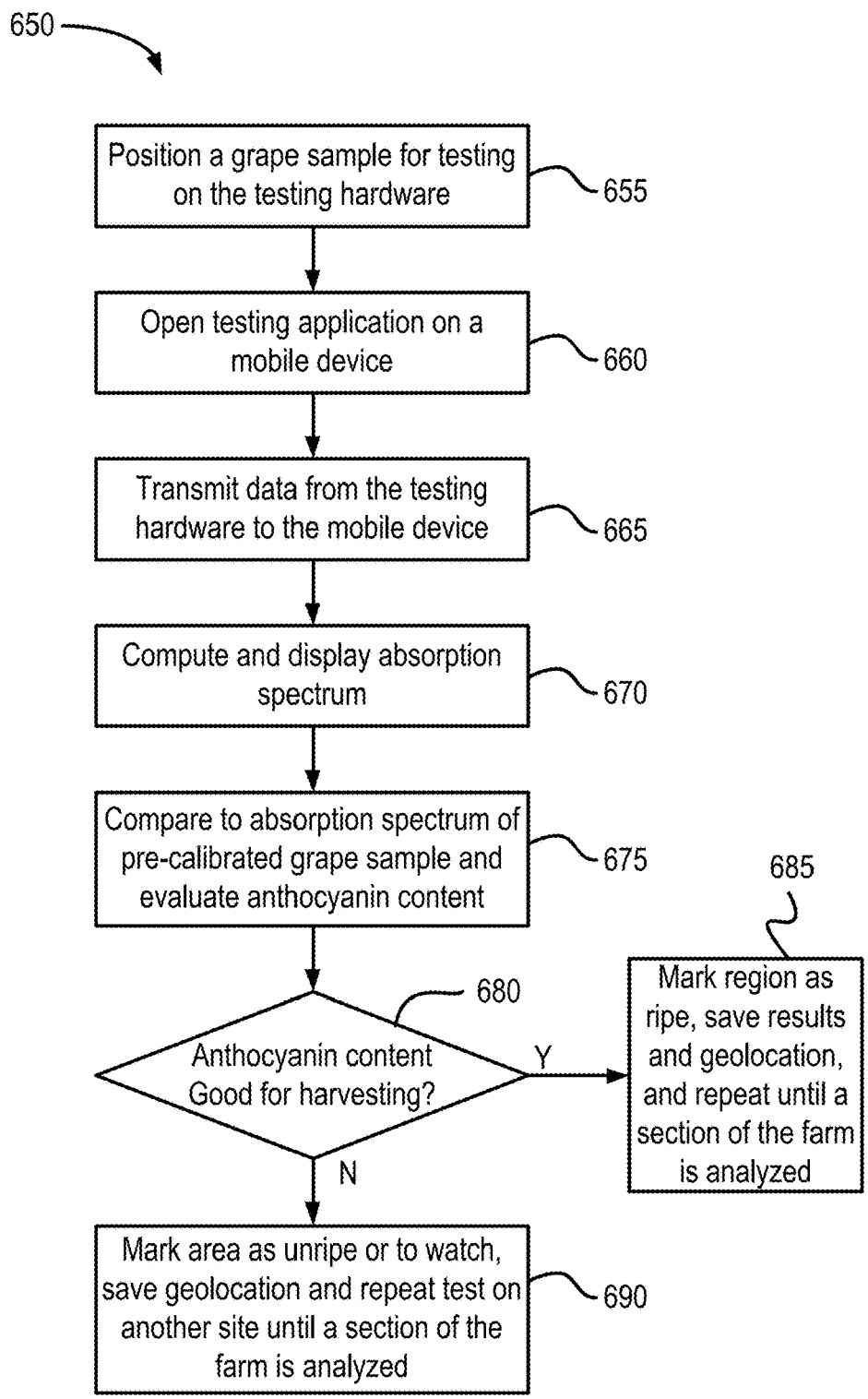
FIG. 6B shows a flow diagram representing an example process for operating the testing system shown in FIG. 6A.

FIG. 6A shows a testing system 600 for measurement of anthocyanin levels in a grape sample 604 using a testing apparatus similar to the one shown in FIG. 1. FIG. 6B shows a flow diagram 650 representing an example process for operating the testing system 600 shown in FIG. 6A. FIG. 6A also shows example representations of status of a mobile device 122 corresponding to one or more stages of the process 650. The device enclosure 602 shown in FIG. 6A differs from the device enclosure 102 shown in FIG. 1 in that, while the enclosure 102 in FIG. 1 included a sample slot 118 for receiving a vail, the enclosure 602 shown in FIG. 6A includes a curved receiving surface for receiving a grape 604. The curved receiving surface allows for grapes of various sizes to be easily tested. In addition, the position of the light source 114 is relatively closer to the spectrometer 104 than that of the light source 114 in FIG. 1. The location of the light source 114 near the spectrometer 104 allows improvement in the amount of light that is incident on the spectrometer 104 even if the grape being tested is thick, compared to that if the light source were to be positioned as shown in FIG. 1. It should be noted, however, the testing apparatus 100 shown in FIG. 1 could also be used, where the grape to be tested can be placed in the sample slot 118, and any reduction in the intensity of the incident light on the spectrometer 104 can be mitigated by increasing the intensity of light emitted by the light source 114.

Anthocyanin in wine grapes is a pigment responsible for the deep red color in wines and is also an antioxidant. Grape farmers typically look for the anthocyanin content before harvesting among sugar and other parameters. The anthocyanin content of a grape sample is an important factor, as it imparts rich color to the wine. Winemakers generally keep the skin in contact with the pulp, a process called maceration, to obtain the deep red color. The skin is rich in anthocyanin and if harvested optimally, it can lead the desired color. For a winemaker, this can determine if the wine batch is a regular or a premium batch which can yield significantly higher returns. Currently, the measurement of anthocyanin is done in labs, which is a slow and expensive process. The system and process discussed below in relation to FIGS. 6A and 6B perform anthocyanin testing on a smartphone in the farm and construct geospatial maps across the entire farm. This can be done by relatively unskilled workers (e.g., not a lab technician) who can operate and app to capture the anthocyanin content. A GPS system on the phone can simultaneously capture the position and create a map. The farmer of winemaker can then figure out regions of the farm that need to be harvest and regions that need to be watched. Providing this information can be beneficial for harvesting and can in turn fetch higher returns.

Stages 655, 660, 665, and 670 of the process are similar to the corresponding process stages of the processes discussed above, and are not discussed in further detail. In stage 675, the grape testing application can compare the absorption spectrum of the grape sample 604 with stored absorption spectra. The stored absorption spectra can have known corresponding anthocyanin levels. In addition the stored absorption spectra can be specific to grape types, such as cabernet, merlot, shiraz, etc. The grape testing application can find a matching stored absorption spectra corresponding to the grape 604 being tested. If a match is found, the application can estimate that the anthocyanin level of the tested grape sample is equal to the anthocyanin level of the matched stored absorption spectrum. The estimated anthocyanin level can be displayed on the display screen of the mobile device 122 as shown in FIG. 6A(iii). The process 650 further includes determining (stage 680) whether the estimated anthocyanin level is above, below, or at a desired level. In some implementations, the application can classify the measured levels of anthocyanin as being in a high range, a mid range, or a low range. The application can also classify the anthocyanin level as ripe or unripe (stages 685 and 690). The application can store the geolocation of the portion of the farm from where the grape being tested was acquired along with the classification. The application can test grapes of other portions of the farm and display the geolocation and the corresponding estimated classification to the user on the display device of the mobile device, as shown in FIG. 6A(iv) and (v). The application can also indicate whether the grapes in a portion of the farm are ready to harvest using check marks, as shown in FIG. 6A(v). While the grape testing application discussed above is shown to be running on a mobile device 122, the application can also run on a laptop, a personal digital assistant, a tablet, a laptop, or a personal computer.

Figure 7A:
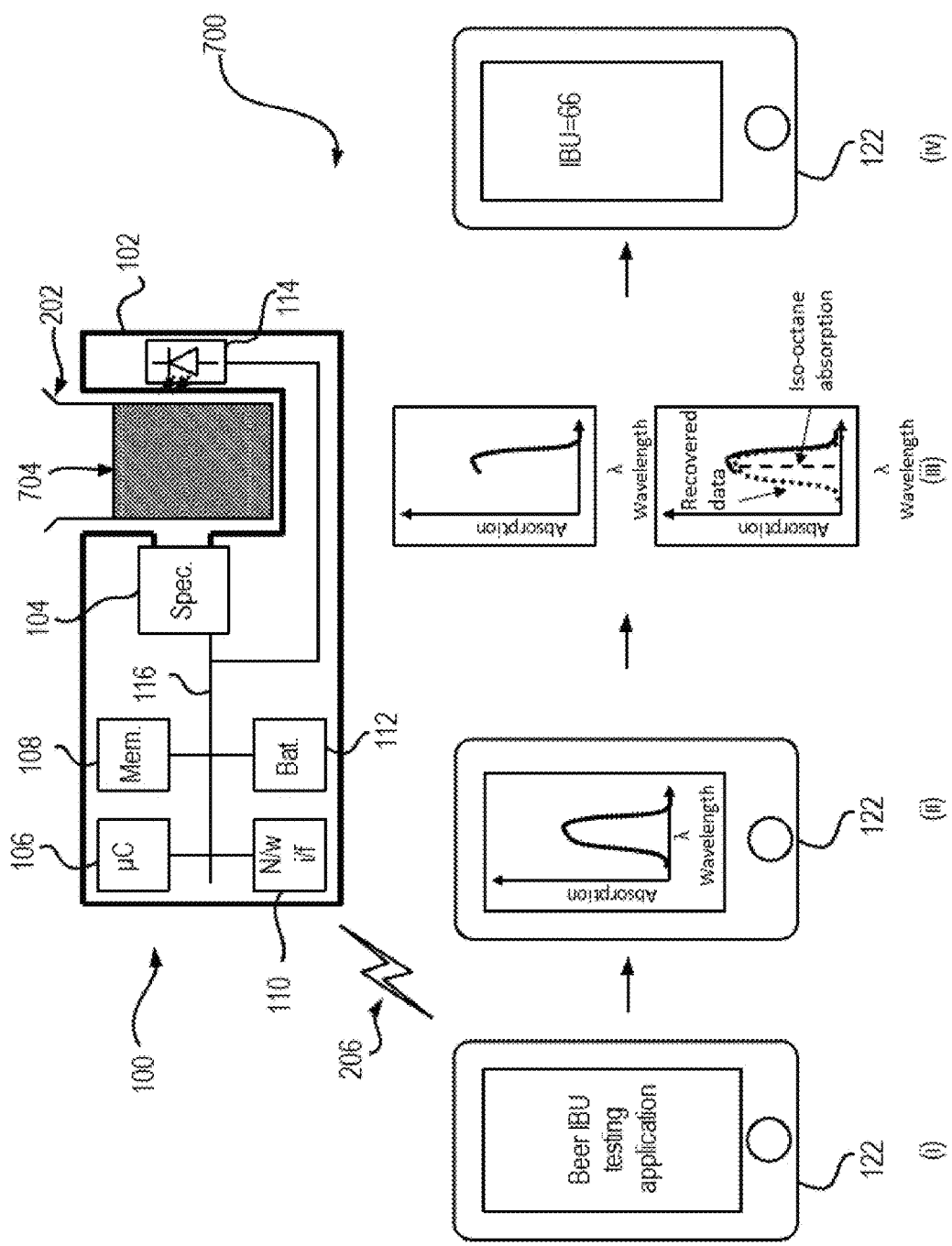
FIG. 7A shows a testing system for measurement of international bitterness units (IBU) of a beer sample using the testing apparatus shown in FIG. 1.
Figure 7B:
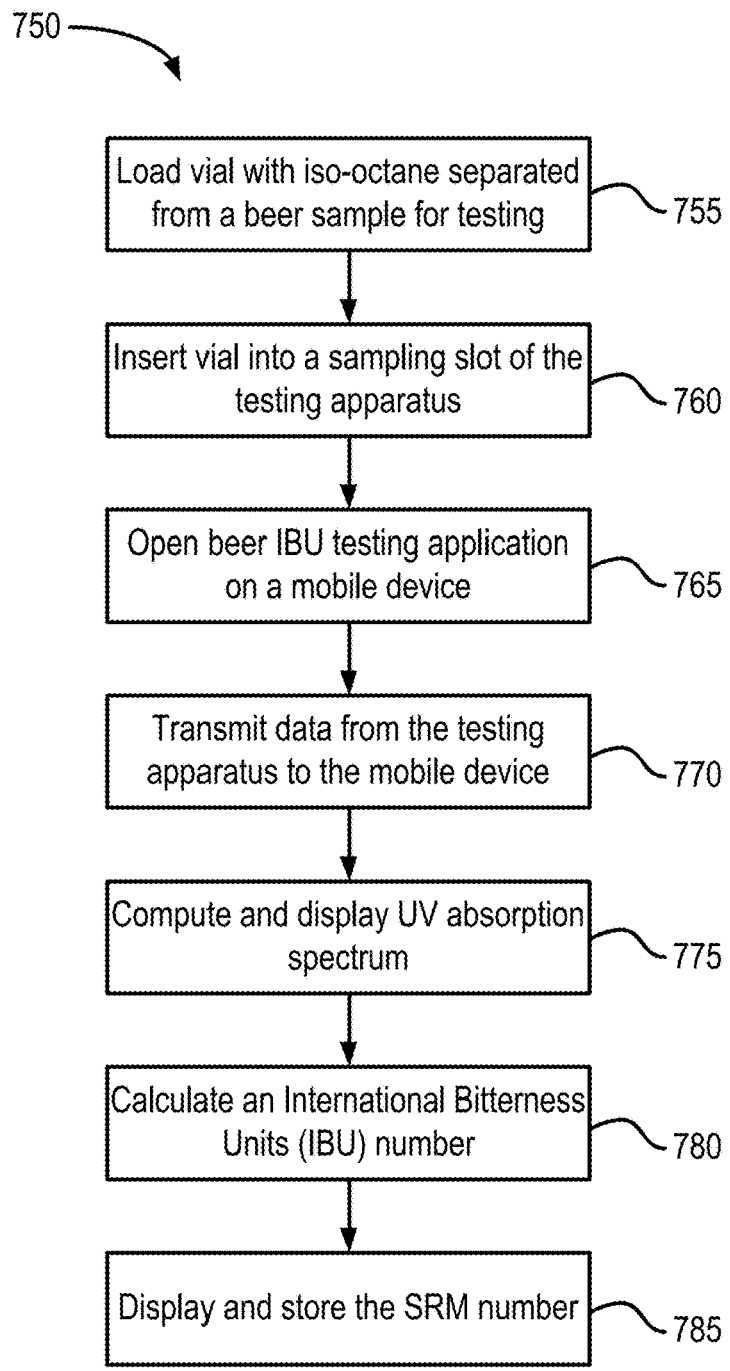
FIG. 7B shows a flow diagram representing an example process for operating the testing system shown in FIG. 7A.

FIG. 7A shows a testing system 700 for measurement of international bitterness units (IBU) of a beer sample using the testing apparatus 100 shown in FIG. 1. FIG. 7B shows a flow diagram 750 representing an example process for operating the testing system 700 shown in FIG. 7A. FIG. 7A also shows example representations of status of a mobile device 122 corresponding to one or more stages of the process 750. The IBU for beer is an industry standard for the bitterness of beer or the concentration of isohumulones in the hops that are involved in the brewing process. The IBU number is calculated by separating the organic components in the beer sample by a centrifugation process and then performing the UV absorption at a particular wavelength, for example, at about 275 nm. In some implementations, the following equation can be used to determine the IBU: IBU=50×Abs. at 275 nm. The IBU is an important distinguishing factor for beer samples as it plays an important role in the final taste of the sample. It can also be used as a metric for repeatability of a recipe which can be useful feedback for a brewer. The system and process discussed below in relation to FIGS. 7A and 7B, IBU measurements are performed on a mobile device platform. In some instances, the spectrometer may be sensitive only up to 312 nm, which is close to the 275 nm target. A Gaussian function can be extrapolated by knowing a few data points in the 312 nm range. By this the same spectrometer that can measure the SRM, wine color tone and intensity, and anthocyanin (discussed above) can be adapted to measure the IBU. Hence, this brings value to a user who can perform multiple tests on a single mobile device platform.

Stages 755, 760, 765, and 770 of the process 700 are similar to the corresponding stages in the processes discussed above, and are not discussed in further detail. At stage 775, the IBU testing application can determine an absorption spectrum of the fluid sample 704 based on the data received from the testing apparatus 100. As mentioned above, in some implementations, the spectrometer 104 may be limited in its sensitivity at and below 312 nm. To determine the absorption level at 275 nm, the application can extrapolate the received absorption data to determine the absorption at 275 nm (as shown in FIG. 7A(iii)). Using the extrapolated absorption level at 275 nm, the application can determine the IBU using the equation mentioned above (stage 780). The application can also display the determined IBU on the display screen of the mobile device 122, as shown in FIG. 7A(iv), and store the IBU level in memory (stage 785).

Figure 8:
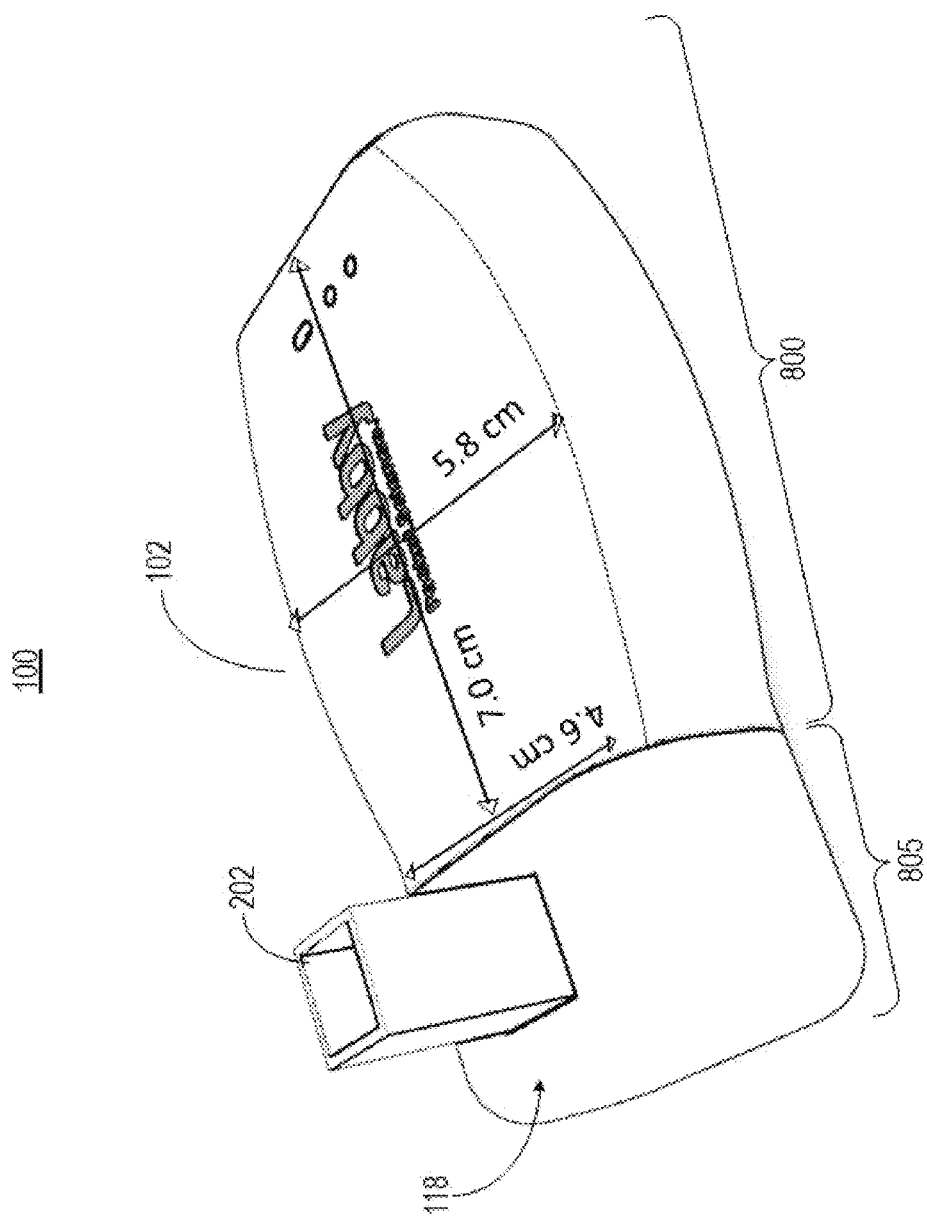
FIG. 8 shows a perspective view of an example implementation of the testing apparatus of FIG. 1.
Figure 9:
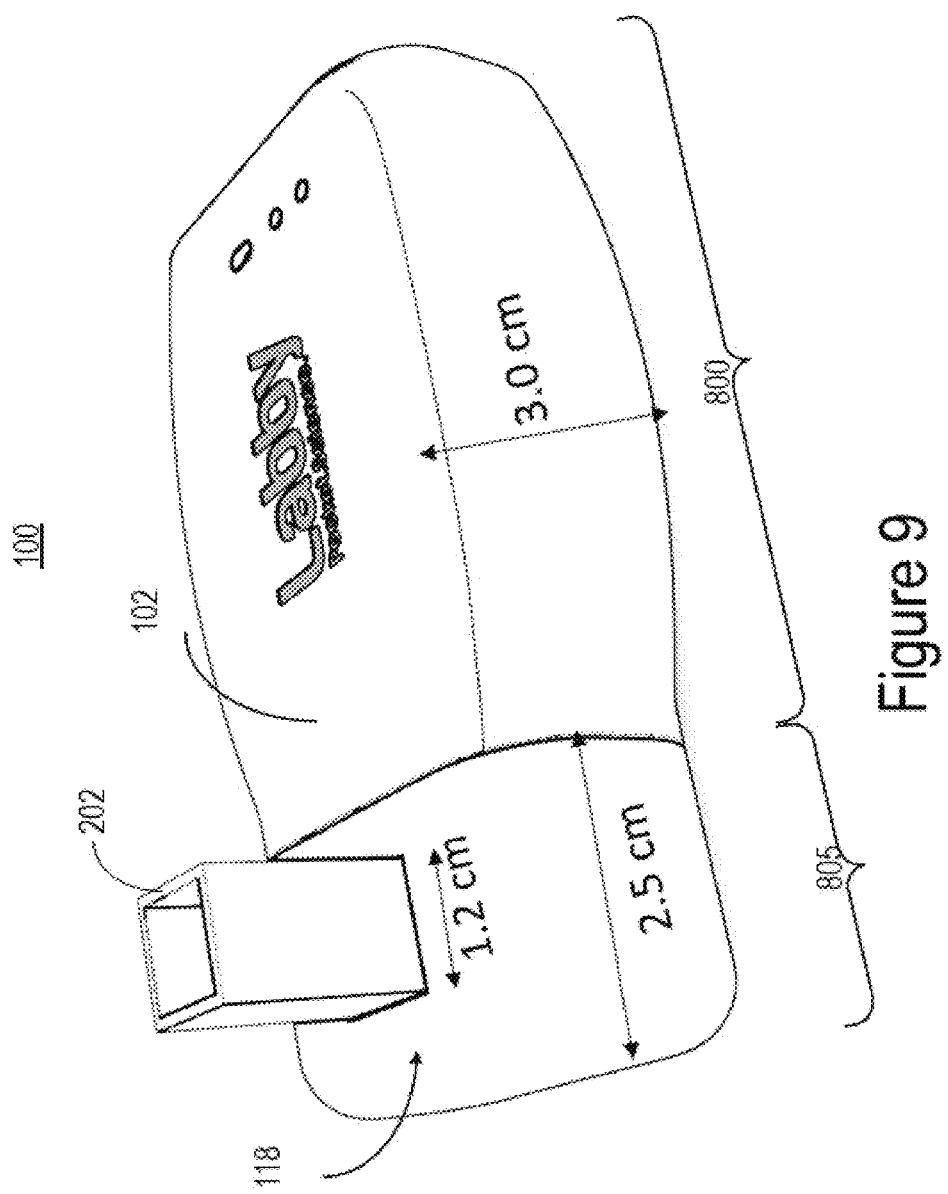
FIG. 9 shows a perspective view of an example implementation of the testing apparatus of FIG. 1.

FIG. 8 shows a perspective view of an example implementation of the testing apparatus 100 of FIG. 1. FIG. 9 shows a perspective view of an example implementation of the testing apparatus 100 of FIG. 1. Referring to FIGS. 8 and 9, the testing apparatus 100 can include an enclosure 102 that houses the components illustrated in the block diagram of FIG. 1, such as the at least one spectrometer 104, the at least one microcontroller 106, the at least one memory 108, the at least one network interface 110, the at least one battery 112 (or other power source), the at least one light source 114, and the at least one communication bus 116. The device enclosure 102 also includes the at least one sample slot 118. In FIGS. 8 and 9, a vial 202 is shown inserted into the sample slot 118. For example, the vial 202 can be configured to contain a sample fluid to be tested, such as beer, wine, or milk.

FIGS. 8 and 9 illustrate one example physical form factor for the testing apparatus 100. As shown, the testing apparatus 100 can have two separate portions, which may be referred to as a body portion 800 and a head portion 805. The body portion 800 and the head portion 805 can be coupled to one another, such that together, the body portion 800 and the head portion 805 form the enclosure 102 in which the various components described above are housed.

The body portion 800 and the head portion 805 can be formed separately, and may be detachable or removable from one another. For example, the body portion 800 and the head portion 805 may be press fit or friction fit to one another, and a user may separate the body portion 800 from the head portion 805 by pulling the body portion 800 away from the head portion 805. The body portion 800 and the head portion 805 may also be attached to one another by use of a mechanical fastener, such as a clamp, a bolt, etc. Similar to a friction fit implementation, such a mechanical fastener may be configured to be removed by a user, such that the body portion 800 and the head portion 805 are removably attached to one another.

The testing apparatus 100 can have a physical shape that facilitates portability and easy operation of the testing apparatus 100. For example, the dimensions of the testing apparatus 100 can be selected to allow the testing apparatus 100 to be handheld (e.g., held by a user using one hand or two hands during operation) and easy to store and carry. Thus, as shown, the testing apparatus 100 may have a shape in which various edges, such as the edges along the length of the body portion 800, have a curved shape selected to be comfortable during handheld use. Also as shown, the body portion may have a length of 7.0 centimeters, a width of 5.8 centimeters, and a height of 3.0 centimeters, while the head portion 805 may have a length of 2.5 centimeters, a width of 4.6 centimeters, and height equal to the height of the body portion 800 (i.e., 3.0 centimeters). However, the dimensions shown in FIGS. 8 and 9 are illustrative only, and the testing apparatus 100 may be designed with dimensions different from those shown. For example, the body portion 800 can have a length in the range of 5 centimeters to 10 centimeters, a width in the range of 4 centimeters to 7 centimeters, and a height in the range of 2 centimeters to 4 centimeters, while the head portion 805 can have a length in the range of 2 centimeters to 3 centimeters, a width in the range of 3 centimeters to 4 centimeters, and a height in the range of 2 centimeters to 4 centimeters.

Other dimensional ranges and shapes may also differ from those illustrated. For example, the enclosure 102 of the testing apparatus 100 may have edges and corners that are squared or chamfered, rather than curved as shown. Similarly, while the sample slot 118 is shown as including a square shaped aperture formed through the head portion 805 having edges with a length of 1.2 centimeters, other shapes or dimensions for the aperture can be selected. For example, the sample slot 118 may instead have a circular or oval shape, and may have a diameter in the range of 0.8 centimeters to 1.5 centimeters. In implementations in which the sample slot 118 is configured to receive the vial 202, the shape and dimensions of the sample slot 118 may be selected to be approximately equal to the cross-sectional shape and dimensions of the vial 202. However, as described further below, the head portion 805 may instead have a sample slot 118 or other aperture or opening configured to receive a fluid sample in a variety of other ways that may not make use of the vial 202. The testing apparatus 100 may include a variety of different head portions 805 and a single body portion 800, and the user may select an appropriate head portion 805 based on the fluid to be tested, for example.

Figure 10:
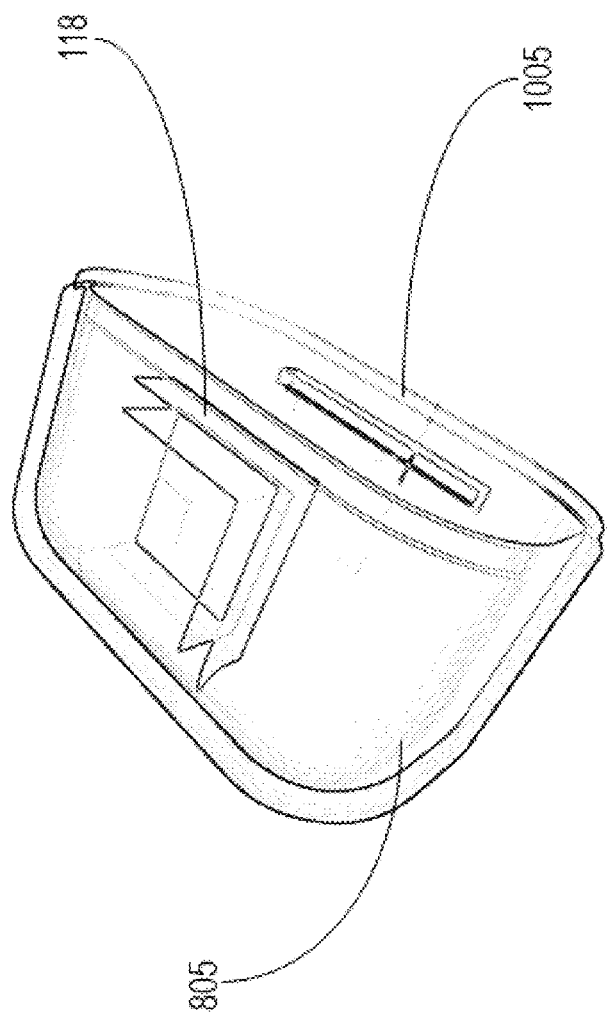
FIG. 10 shows a perspective view of a head portion of the example testing apparatus shown in FIG. 8.

FIG. 10 shows a perspective view of a head portion 805 of the example testing apparatus 100 shown in FIG. 8. As described above in connection with FIGS. 8 and 9, the head portion 805 includes a sample slot 118 having a square shaped aperture formed at a top surface of the head portion 805 and extending partially through the head portion 805. In addition, the head portion 805 includes another slot 1005 positioned near a bottom surface of the head portion 805. FIG. 10 shows the head portion 805 as partially transparent for illustrative purposes, however in some implementations, the slot 1005 may not be visible from outside the head portion 805. The slot 1005 can be used to secure an attachment mechanism configured to transport a fluid sample into the sample slot 118, as described further below in connection with FIGS. 11 and 12.

Figure 11:
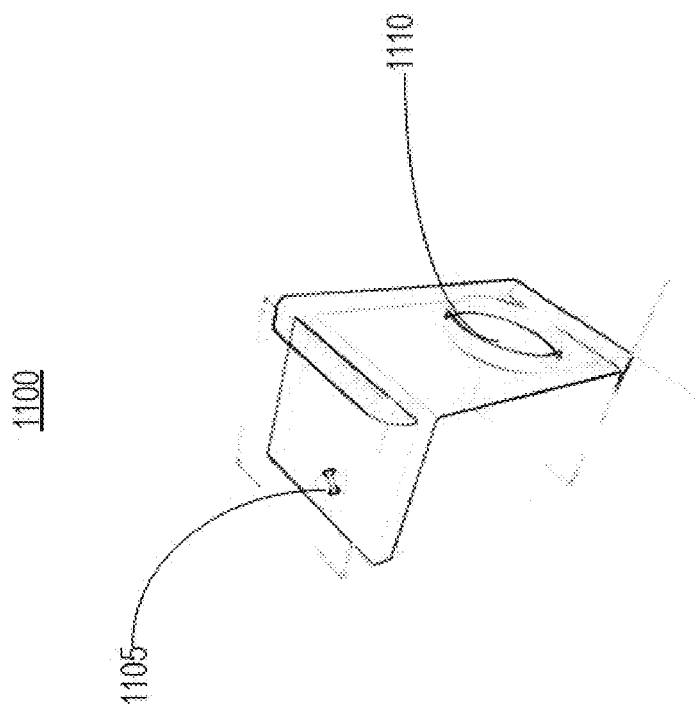
FIG. 11 shows a perspective view of a capillary attachment that can be used with the example testing apparatus of FIG. 8.
Figure 12:
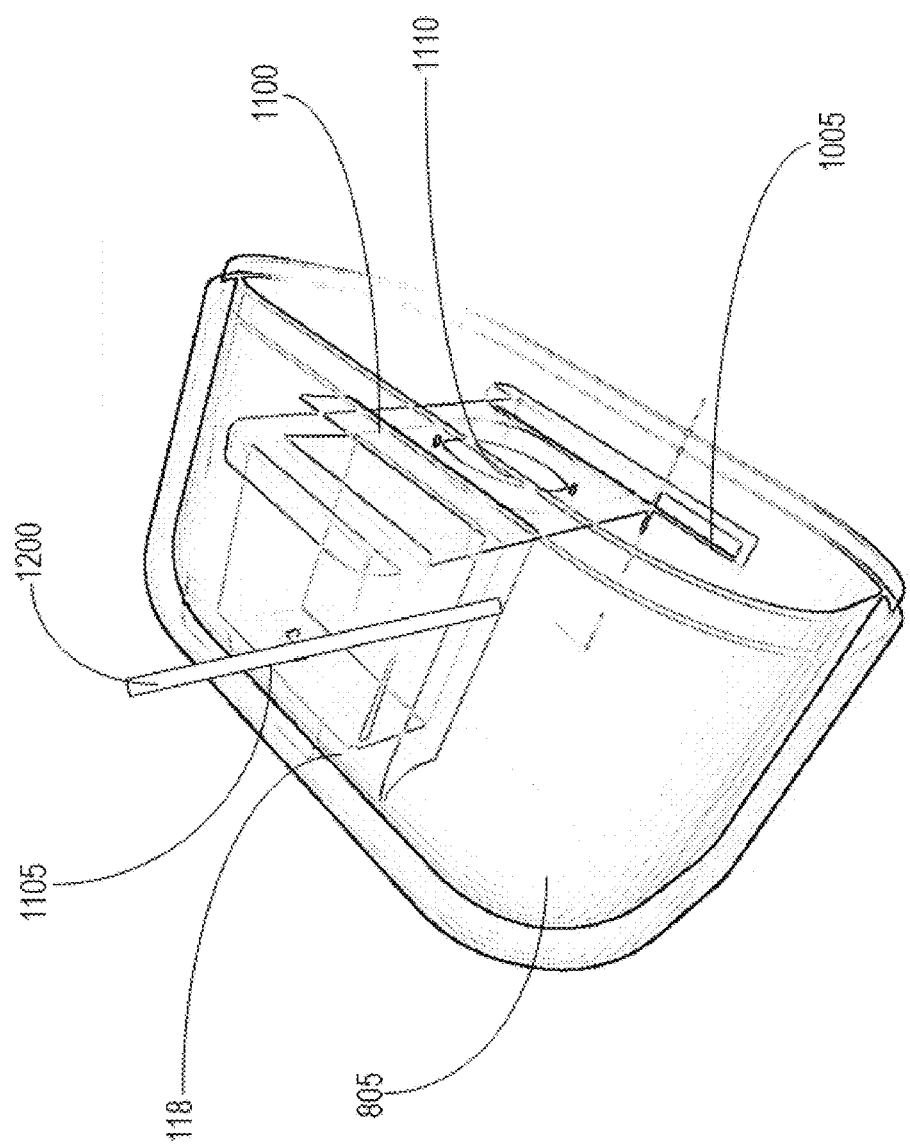
FIG. 12 shows a perspective view of the capillary attachment of FIG. 11 inserted into the head portion of FIG. 10.

FIG. 11 shows a perspective view of a capillary attachment 1100 that can be used with the example testing apparatus 100 of FIG. 8. FIG. 12 shows a perspective view of the capillary attachment 1100 of FIG. 11 inserted into the head portion 805 of FIG. 10. Referring to FIGS. 11 and 12, the capillary attachment 1100 can be used to draw fluid into the sample slot 118 of the head portion 805 of the testing apparatus 100 via capillary action (which can also be referred to as capillarity, the capillary effect, or wicking). For example, the capillary attachment 1100 is configured to receive a capillary tube 1200 as shown in FIG. 12. Together, the capillary attachment 1100 and the capillary tube 1200 can take the place of the vial 202 illustrated in FIGS. 8 and 9. As shown in FIG. 11, the capillary attachment 1100 can be an L-shaped component having a first opening 1105 formed through a top surface of the capillary attachment 1100 and a second opening 1110 formed through a side surface of the capillary attachment 1100. The first opening 1105 can be configured to receive the capillary tube 1200.

The capillary tube 1200 can have a diameter suitable for drawing fluid into the capillary tube 1200 via capillary action. For example, the capillary tube 1200 can have a diameter in the range of 1.2 millimeters to 1.4 millimeters. The opening 1105 can have a diameter selected to accommodate the capillary tube 1200. For example, the diameter of the opening 1105 can be slightly larger than the diameter of the capillary tube 1200, such as 1.5 millimeters. In some implementations, the diameter of the opening 1105 can be in the range of 1 millimeter to 1.5 millimeters. The opening 1110 can be configured to avoid interfering with light generated by the light source 114 and used by the spectrometer 104. For example, the opening 1110 can be positioned such that, when the capillary attachment 1100 is installed in the testing apparatus 100, the opening 1110 is in alignment with the opening 128 formed through the enclosure 102 as shown in FIG. 1.

As illustrated in FIG. 12, the capillary attachment 1100 can be secured within the sample slot 118 through use of the slot 1005. For example, the side surface of the capillary attachment 1100 can be inserted into the slot 1005 when the capillary attachment 1100 is inserted into the sample slot 118. Thus, the capillary attachment 1100 can be secured within the slot 1005, thereby providing stability of the capillary attachment 1100 within the sample slot 118. The capillary tube 1200 can then be inserted through the opening 1105 and can be used to draw fluid into the sample slot 118. For example, the capillary tube 1200 can be placed into a container containing the sample fluid and can draw a portion of the sample fluid down the capillary tube 1200 and into the sample slot 118 via capillary action. The capillary attachment 1100 may be configured to be easily removed from the head portion 805. For example, the capillary attachment 1100 may be secured within the slot 1005 via press fit or friction fit, such that a user can easily remove the capillary attachment 1100 by pulling it out of the slot 1005. Thus, the user can switch between a configuration that makes use of the vial 202 or a configuration that makes use of the capillary tube 1200.

Figure 13:
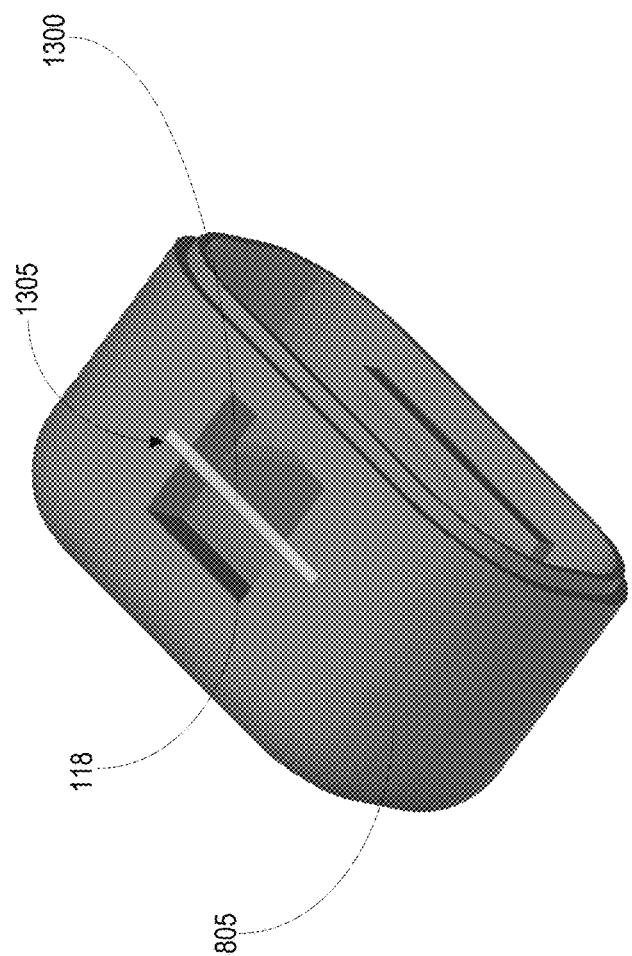
FIG. 13 shows a perspective view of the head portion of FIG. 10 containing a slide.
Figure 14:
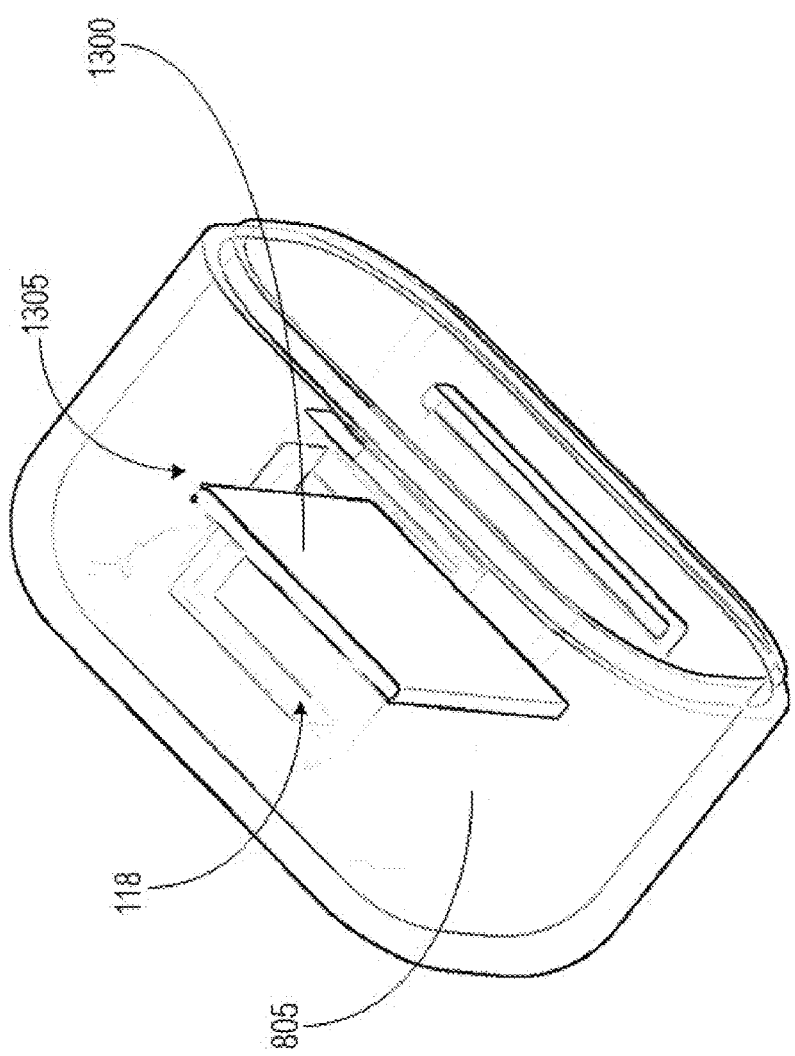
FIG. 14 shows a perspective view of the head portion of FIG. 10 containing a slide.

FIG. 13 shows a perspective view of the head portion 805 of FIG. 10 containing a slide 1300. FIG. 14 shows a perspective view of the head portion 805 of FIG. 10 containing a slide 1300. Referring to FIGS. 13 and 14, the slide 1300 can be formed from an optically transparent material, such as glass. The slide 1300 can be configured to serve as a surface on which the fluid sample to be tested can be positioned. For example, a user can apply the fluid sample as a coating to the slide 1300, and the slide 1300 can be inserted into the head portion 805 for testing. As shown, the slide 1300 can be inserted into the sample slot 118. However, the sample slot 118 may include a square or rectangular aperture having sides whose lengths are less than a length of the slide 1300. In order to accommodate the slide 1300, the a slot 1305 can extend outwards from opposing edges of the aperture of the sample slot 118, as shown in FIGS. 13 and 14. For example, the slot 1305 can have a length substantially equal to the length of the slide 1300. As a result, the slide 1300 can be inserted into the slot 1305 and secured within the slot 1305 via press fit or friction fit. For example, the slide 1300 can be inserted to a depth that allows a top surface of the slide 1300 to be flush with a top surface of the head portion 805, such that a majority of the surface area of the slide 1300 is located within the sample slot 118 as shown in FIG. 14. FIG. 14 shows the head portion 805 as being partially transparent for illustrative purposes.

The glass slide can have a length in the range of 20 millimeters to 30 millimeters, a width in the range of 20 millimeters to 30 millimeters, and a thickness in the range of 0.15 millimeters to 1.2 millimeters. Thus, the slot 1305 can also have a length in the range of 20 millimeters to 30 millimeters (e.g., selected to match the length of the slide 1300) and a width in the range of 0.15 millimeters to 1.2 millimeters (e.g., selected to match the thickness of the slide 1300). After testing has been completed, a user may remove the slide 1300 from the sample slot 118 by simply pulling the slide 1300 upwards, away from the top surface of the head portion 805.

Figure 15:
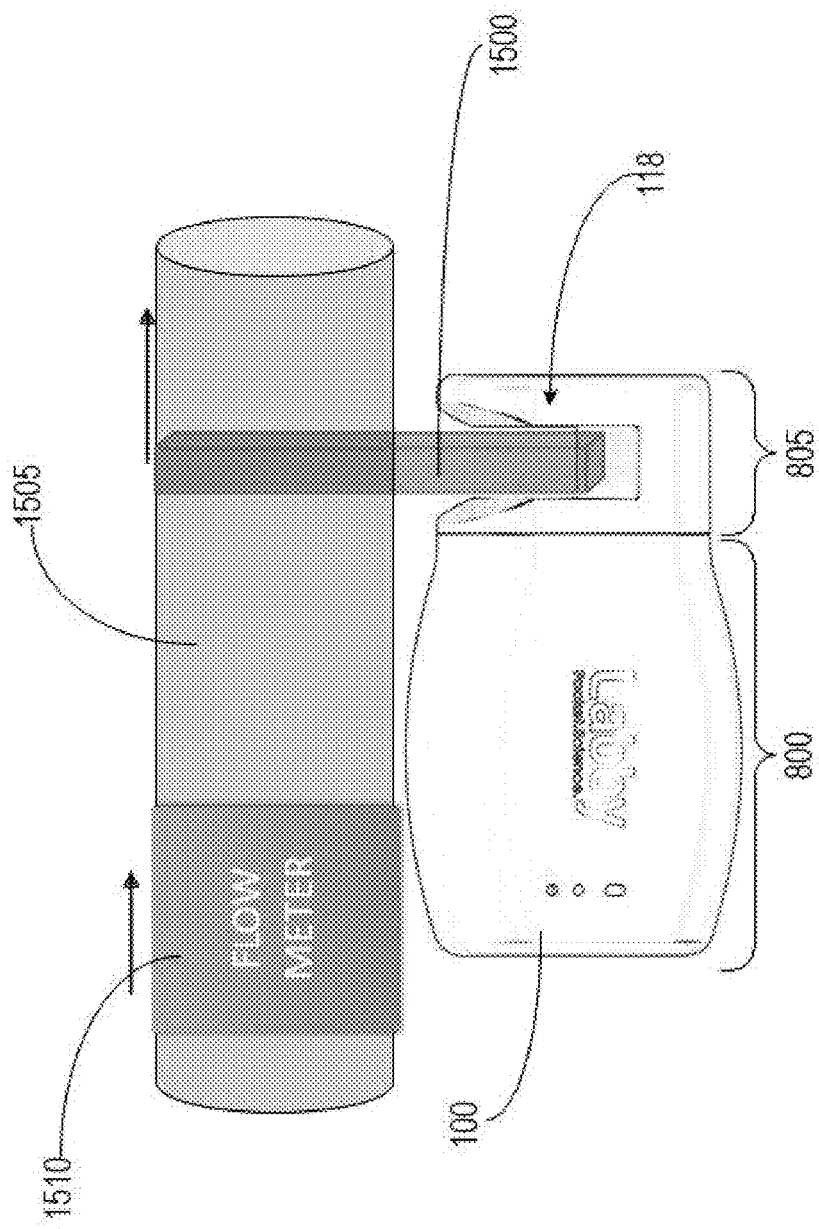
FIG. 15 shows a perspective view of the testing apparatus of FIG. 8 coupled to a pipe that transports a fluid.
Figure 16:
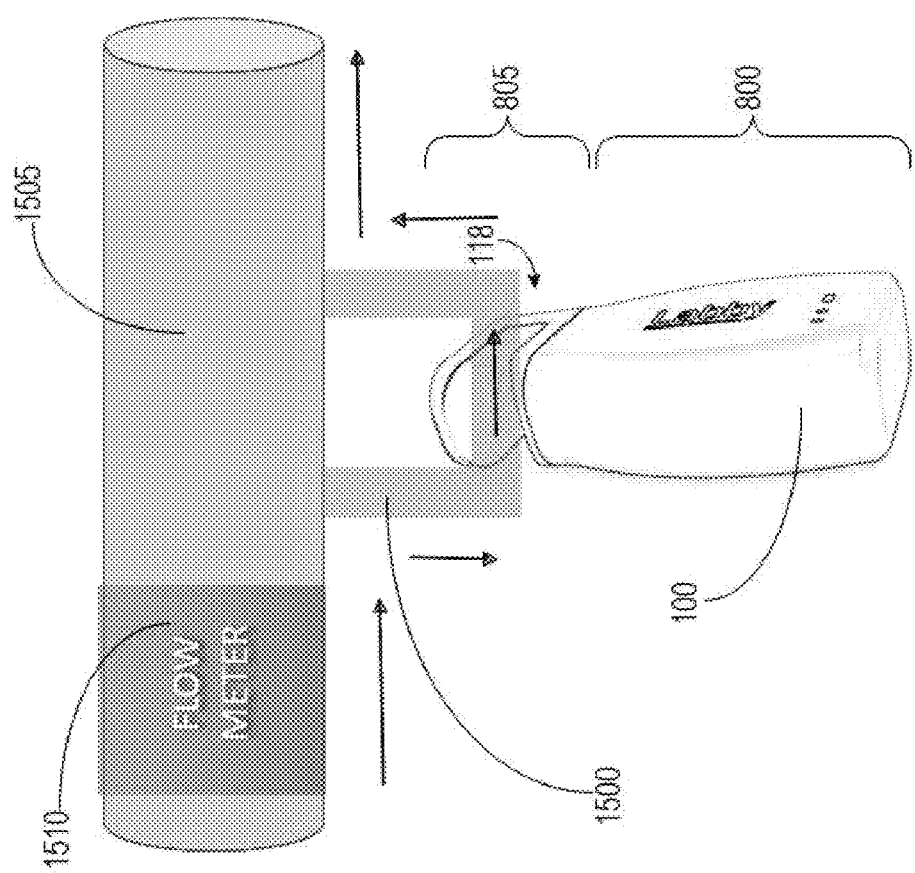
FIG. 16 shows a perspective view of the testing apparatus of FIG. 8 coupled to a pipe that transports a fluid.
Figure 17:
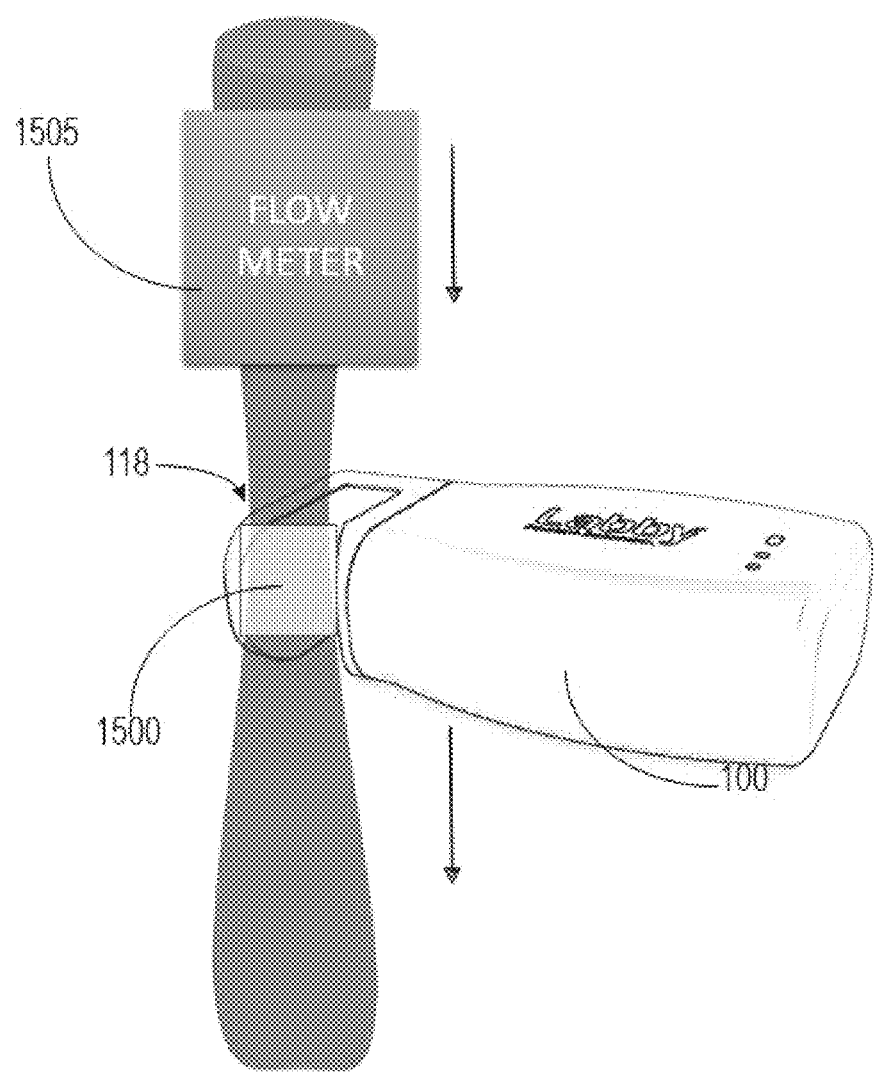
FIG. 17 shows a perspective view of the testing apparatus of FIG. 8 coupled to a pipe that transports a fluid.

FIG. 15 shows a perspective view of the testing apparatus 100 of FIG. 8 coupled to a pipe 1505 that transports a fluid. FIGS. 16 and 17 show similar components arranged differently. Referring generally to FIGS. 15-17, the testing apparatus 100 can be used as shown to measure fluid properties in an industrial setting, such as a factory, a farm, or a milk collection center. For example, the pipe 1505 can be a component of such an industrial facility, and can be modified with a feed tube 1500 to facilitate testing of the fluid transported by the pipe 1505. For example, in a large farm with several milking machines, it may not be practical to take measurements of all of the collected milk by hand. To address this challenge challenges the arrangements of FIGS. 15-17 can include an in-line milk quality sensor that can be integrated into milking machines or other industrial equipment to seamlessly provide data on a regular basis. The arrangement shown in FIGS. 15-17 can include modifications to an existing milking machine or other industrial equipment to have a transparent optical window (i.e., the feed tube 1500) where the testing apparatus 100 can be permanently integrated or attached every time an operation is carried out. The optical window enables the light signal from the testing apparatus 100 to pass through the flowing fluid sample (e.g., a milk sample) and the resultant scattering, absorption, and fluorescence can then captured using the testing apparatus 100. These custom attachments can be integrated into standard milking machines that are semi- or fully automated, or have robotic milking functionality.

Referring again to FIG. 15, the testing apparatus 100 is coupled to the pipe 1505 by a feed tube 1500. Stated differently, the feed tube 1500 is in fluidic communication with both the testing apparatus 100 and the pipe 1505, and the feed tube 1500 is configured to divert at least a portion of the fluid flowing through the pipe 1505 into the testing apparatus 100. The head portion 805 of the testing apparatus 100 shown in FIG. 15 is configured to receive the feed tube 1500, rather than a vial (such as the vial 202 shown in FIGS. 8 and 9), a capillary attachment (such as the capillary attachment 1100 shown in FIG. 11), or a slide (such as the slide 1300 shown in FIG. 13). As a result, the head portion 805 shown in FIG. 15 can be shaped differently than the head portions 805 described above. For example, the feed tube 1500 can be substantially larger than the vial 202. To accommodate the larger size of the feed tube 1500, the aperture of the sample slot 118 not only extends downwards into the head portion 805, but also extends laterally through an entirety of the head portion 805 along a direction parallel to the height of the head portion (as illustrated in FIGS. 8 and 9).

In the arrangement shown in FIG. 15, fluid can flow through the pipe 1505 in a direction from left to right. A portion of the fluid flows into the feed tube 1500 and is then delivered to the testing apparatus 100. The pipe 1505 can be included, for example, in a manufacturing facility in which the sample fluid is produced. For example, the pipe 1505 can be a component of an industrial fluid processing plant for producing or processing fluids such as beer, wine, or milk. Because the feed tube 1500 can divert some of the fluid flowing through the pipe 1505 to the testing apparatus 100, the arrangement can allow for ease of testing sample fluids during a manufacturing process. The flow meter 1510 can be configured to determine a rate at which fluid flows through the pipe 1505. The flow meter 1510 can also be configured to provide flow rate information to the testing apparatus 100. For example, the flow meter 1510 can be or can include an electronic device configured to communicate with the testing apparatus 100 via the network interface 110 shown in FIG. 1. The testing apparatus 100 can store flow rate information received from the flow meter 1510, for example in the memory 108. The flow rate information can then be referred to later when the spectral data is collected and analyzed. For example, the flow rate of fluid in the pipe 1505 can be correlated with measurement values obtained by processing the spectral data in order to determine acceptable ranges for the flow rate (i.e., ranges for the flow rate that tend to produce fluid samples having more desirable spectral data).

FIG. 16 shows a perspective view of the testing apparatus 100 of FIG. 8 coupled to a pipe 1505 that transports a fluid. The testing apparatus 100 of FIG. 16 is similar to that shown in FIG. 15. However, the arrangement of the pipe 1505 and the feed tube 1500 of FIG. 16 differs from that shown in FIG. 15. For example, in FIG. 16, the feed tube 1500 diverts fluid from the pipe 1505, but also returns the diverted fluid to the pipe 1505. Thus, the sample fluid flows through the feed tube 1500 in parallel with the fluid flowing through the pipe 1505. As a result, during spectral testing of the sample fluid in the feed tube 1500, the fluid is continuously flowing through the feed tube 1500. To facilitate spectral testing, the feed tube 1500 can be formed from an optically transparent material, such that the feed tube 1500 does not interfere with the spectral data obtained during testing of the sample fluid. This arrangement can help to avoid wasting any of the fluid for testing purposes, as all of the tested fluid is returned to the pipe 1505.

FIG. 17 shows a perspective view of the testing apparatus 100 of FIG. 8 coupled to a pipe 1505 that transports a fluid. The testing apparatus 100 of FIG. 17 is similar to that shown in FIG. 16. However, in FIG. 17, no fluid is diverted from the pipe 1505 for testing purposes. Rather, the tested sample fluid flows through the feed tube 1500 in series with the rest of the fluid flowing through the pipe 1505. Similar to the arrangement of FIG. 16, during spectral testing of the sample fluid in the arrangement of FIG. 17, the fluid is continuously flowing through the feed tube 1500. To facilitate spectral testing, the feed tube 1500 can be formed from an optically transparent material, such that the feed tube 1500 does not interfere with the spectral data obtained during testing of the sample fluid.

Figure 18:
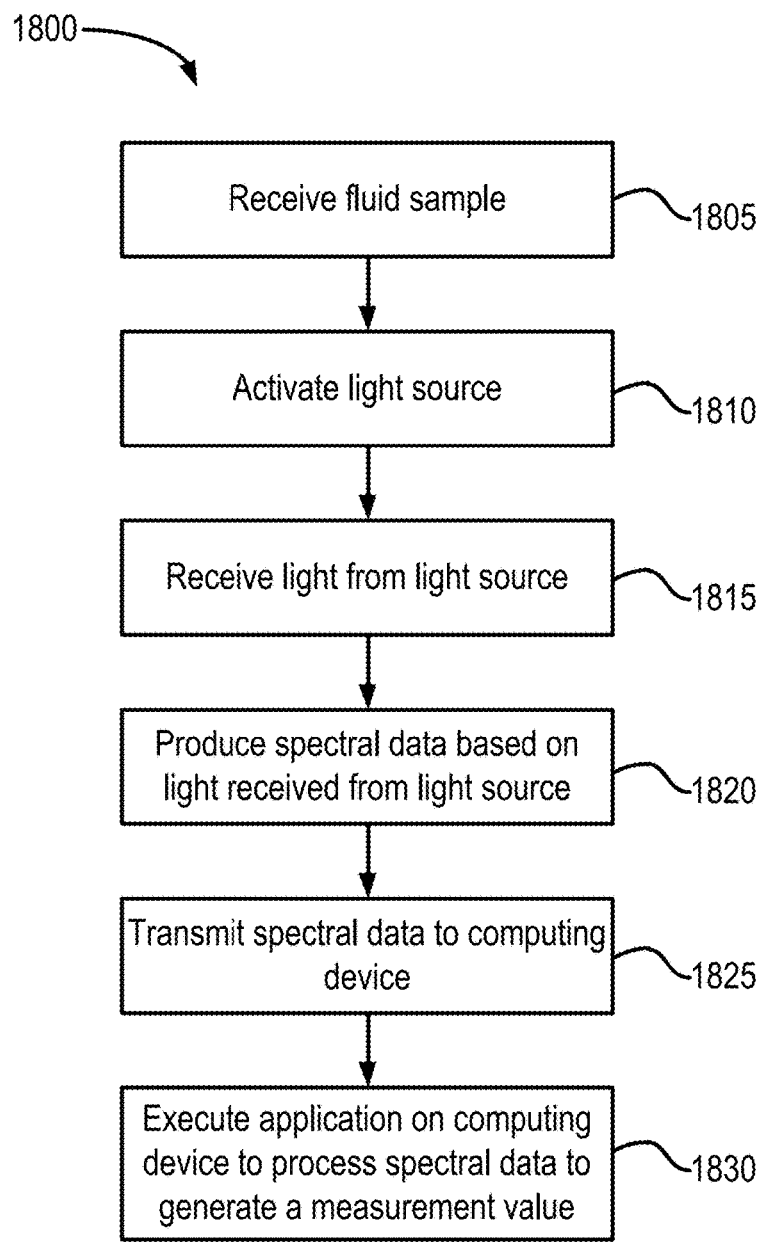
FIG. 18 shows a flow diagram representing an example process of testing sample fluids.

FIG. 18 shows a flow diagram representing an example process 1800 of testing sample fluids. In brief overview, the process 1800 includes receiving a sample fluid (stage 1805), activating a light source (stage 1810), receiving light from the light source (stage 1815), producing spectral data based on the light received from the light source (stage 1820), transmitting spectral data to a computing device (stage 1825), and executing an application on the computing device to process the spectral data to generate a measurement value (stage 1830).

Referring again to FIG. 18, and in greater detail, the process 1800 includes receiving a sample fluid (stage 1805). The sample fluid can be received in a sample aperture or sample slot of a head portion of a portable testing apparatus, such as the testing apparatus 100. Fluid can be introduced into the sample slot or sample aperture in a variety of ways. For example, the sample fluid can be collected in a vial, and the vial can be inserted into the sample slot. The vial can be optically transparent to facilitate collection of spectral data of the sample fluid. The sample fluid can also be introduced into the sample slot or sample aperture via capillary action. For example, a capillary attachment such as the capillary attachment 1100 shown in FIG. 11 can be attached to the head portion of the portable testing apparatus. The capillary attachment can receive a capillary tube such as the capillary tube 1200. The capillary tube can then be placed in fluidic communication with the sample fluid, for example by being immersed in a container containing the sample fluid, and can draw the fluid down the capillary tube into the sample slot or sample aperture via capillary action. The sample fluid can also be received via a slide, such as a glass slide that can be coated with the sample fluid and inserted into the sample slot or sample aperture, as illustrated in FIGS. 13 and 14. The sample fluid can also be received via a feed tube, such as the feed tube 1500 of FIGS. 15-17, that collects fluid from a pipe. The sample fluid can be any type of fluid to be subjected to spectral testing. For example, the sample fluid can be an alcoholic beverage such as beer or wine. The sample fluid can also be milk.

The process 1800 includes activating a light source (stage 1810). The light source can be an LED, a filament bulb, a fluorescent light source, or another form of light source. For example, the light source can be the light source 114 shown in FIG. 1. Activating the light source can cause the light source to provide light having various wavelengths. For example, the light source can provide white light, blue light, green light, red light, or a combination thereof. The wavelength(s) of light emitted by the light source can be selected to be suitable for spectral testing. The light can be directed towards the sample fluid and a spectrometer, such as the spectrometer 104 of FIG. 1. The light source can be included in a head portion of the testing apparatus that also includes the sample slot or sample aperture that receives the sample fluid (stage 1805).

The process 1800 includes receiving light from the light source (stage 1815). The light can be received by the spectrometer. For example, the spectrometer can be positioned opposite from the light source such that at least a portion of the light emitted by the light source can pass through the sample fluid and be incident on the spectrometer. The spectrometer may be included in a body portion of the testing apparatus, coupled to the head portion of the testing apparatus.

The process 1800 includes producing spectral data based on the light received from the light source (stage 1820). The spectrometer can measure the spectral characteristics of the incident light and can produce the spectral data to represent the spectral characteristics. For example, the spectrometer can measure an intensity of one or more wavelengths of the light. The spectrometer can also measure one or more wavelength ranges of the light. The spectral data can be stored locally on the testing apparatus, for example in the memory 108.

The process 1800 includes transmitting spectral data to a computing device (stage 1825). The spectral data can be transmitted, for example, via the network interface 110 through the network 120, as illustrated in FIG. 1. The computing device can be a mobile device, such as a mobile phone or a tablet computing device. The computing device can also be a desktop or laptop computer or a server. The network interface may include a wireless network interface such as a Bluetooth interface. The network interface may include a wired network interface, such as Ethernet or USB. The portable testing apparatus can establish a communication session with the computing device (e.g., by pairing the testing apparatus with the computing device via Bluetooth). Information corresponding to the spectral data can then be transmitted from the portable testing apparatus to the computing device using the communication session.

The process 1800 includes executing an application on the computing device to process the spectral data to generate a measurement value (stage 1830). The application running on the computing device can processes the spectral data to determine a measurement value corresponding to an absorption spectra of the fluid sample. In some implementations, the application (or the testing apparatus itself) can first be calibrated before the spectral data is collected or processed, to help ensure accuracy of the generated measurement value. The measurement value can be an SRM value, which may be calculated using the SRM formula described above in connection with FIGS. 2A and 2B. The measurement value can also include a value associated with a pH level of the sample fluid, wort color of the sample fluid, an international bitterness units measurement of the sample fluid, a tone of the sample fluid, or an intensity of the sample fluid. The application can cause an electronic display of the computing device to display a graphical representation or visualization of the measurement value (or the spectral data itself). In some implementations, the application may compare the generated measurement value to a reference measurement value. For example, a reference measurement value can be a value generated based on spectral data associated with a reference batch of the sample fluid. The comparison of such a value for a new batch to the value for the reference batch can help to determine a level of uniformity across batches. For example, the comparison can reveal whether the new batch and the reference batch are within a specified range of uniformity with respect to at least one characteristic (e.g., a characteristic related to the measurement values being compared).

Figure 19:
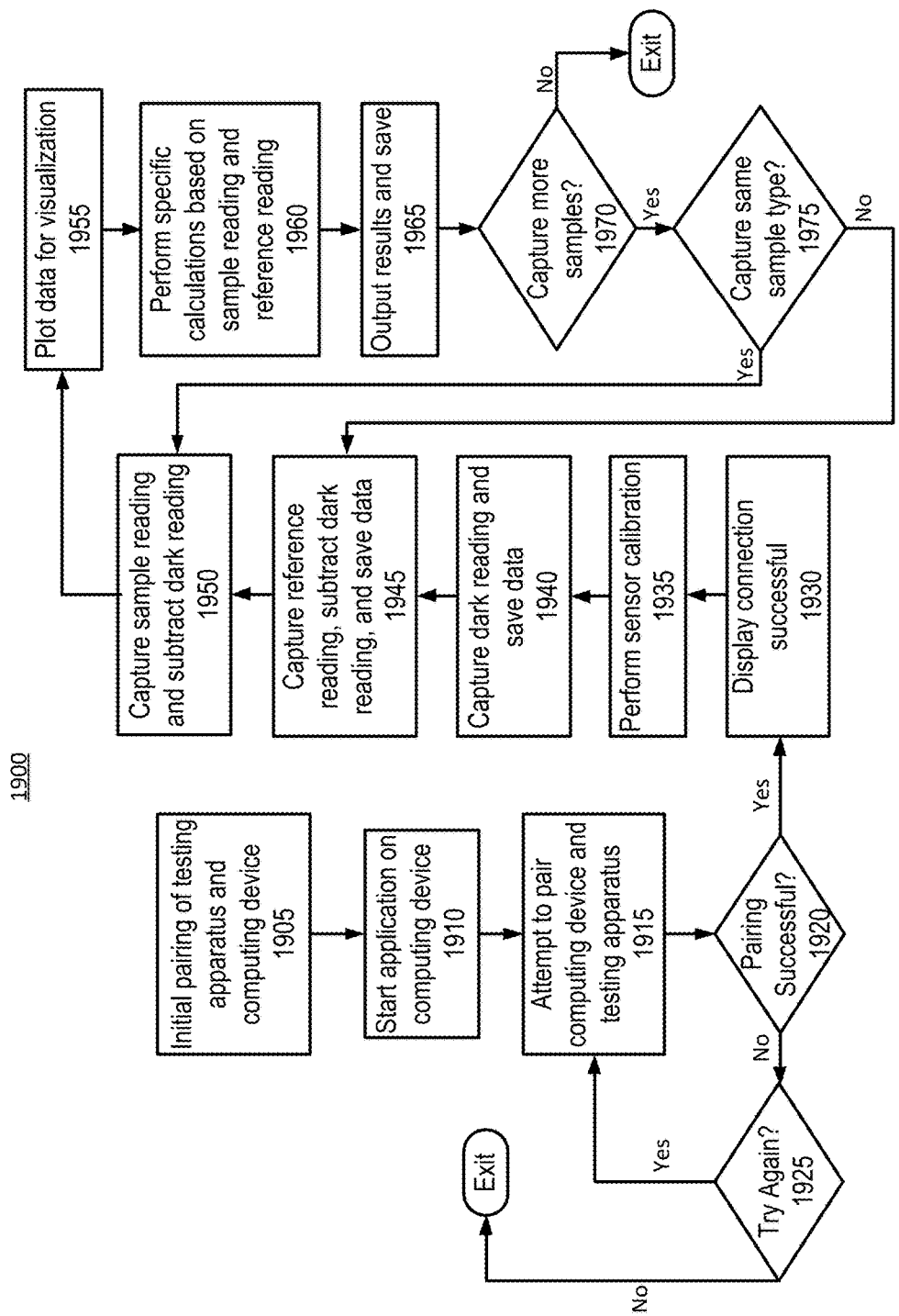
FIG. 19 shows a flow diagram representing an example process of testing sample fluids.

FIG. 19 shows a flow diagram representing an example process 1900 of testing sample fluids. The process 1900 begins at stage 1905, in which an initial pairing of a testing apparatus, such as the testing apparatus 100, and a computing device, such as any one of the mobile phone 122, the laptop computer 124, and the desktop computer 126, is performed. The initial pairing can include a Bluetooth pairing process in which the testing apparatus registers itself with the computing device. In some implementations, a password can be entered (e.g., via an application executing on the computing device) in order to perform the initial pairing. The initial pairing can cause the computing device to store information relating to the testing apparatus, such that the computing device may recognize the testing apparatus in the future to facilitate automatic pairing after the initial pairing.

A fluid testing application can then be started on the computing device at stage 1910. The application can be started, for example, in response to selection of an icon associated with the application by a user of the computing device. Execution of the application can cause the computing device to attempt to pair with the testing apparatus at stage 1915. For example, as described above, the computing device can attempt to pair via a Bluetooth interface with the testing apparatus, and the pairing may occur automatically (e.g., without additional input from a user) in response to execution of the application. At stage 1920, the computing device can determine whether pairing was successful. If pairing was not successful, the process 1900 proceeds to stage 1925. If no additional pairing attempts are to be made, the process 1900 can exit. Otherwise, the process can return to stage 1915 in order for the computing device to attempt again to pair with the testing apparatus. After pairing is successful at stage 1920, the process 1900 proceeds to stage 1930, in which the computing device can display a message or other indication that the pairing process resulted in a successful connection established between the computing device and the testing apparatus.

At stage 1935, sensor calibration is performed. Sensor calibration can include calibration of any of the components of the testing apparatus, such as calibration of the spectrometer or the light source. For example, the testing apparatus can store instructions for performing a calibration routine, and the computing device can transmit a command to the testing apparatus (e.g., via the Bluetooth connection or other connection established as part of the pairing stage 1915) to cause the testing apparatus to perform the calibration routine. After calibration is complete, the testing apparatus can capture a dark reading at stage 1940. The dark reading can correspond to the generation of spectrometry data either without illumination of the light source of the testing apparatus, without any sample fluid present, or without both illumination of the light source or a sample fluid present. The dark reading can be triggered by information sent from the computing device to the testing apparatus. For example, the computing device can send a particular byte of information to the testing apparatus to cause the testing apparatus to capture the dark reading. The testing apparatus can store the data for the dark reading, and can also transmit the data for the dark reading to the computing device, which also may store the data for the dark reading.

At stage 1945, the testing apparatus can capture a reference reading. The reference reading can correspond to the generation of spectral data for a reference sample fluid. For example, the reference sample fluid can include a batch of fluid (e.g., beer, wine, or milk) whose characteristics are already known. Also at stage 1945, the dark reading can be subtracted from the reference reading. The reference reading can be triggered by information sent from the computing device to the testing apparatus. For example, the computing device can send a particular byte of information to the testing apparatus to cause the testing apparatus to capture the reference reading. The subtraction of the dark reading from the reference reading can be performed by the testing apparatus or by the computing device, and either or both of the testing apparatus and the computing device can store the data after the dark reading has been subtracted.

At stage 1950, the testing apparatus can capture a sample reading. The sample reading can correspond to the generation of spectral data for a sample fluid that is to be compared to the reference sample fluid. For example, the sample fluid can include a new batch of fluid whose characteristics relative to those of the reference fluid are not yet known. Also at stage 1950, the dark reading can be subtracted from the sample reading. The sample reading can be triggered by information sent from the computing device to the testing apparatus. For example, the computing device can send a particular byte of information to the testing apparatus to cause the testing apparatus to capture the sample reading. The subtraction of the dark reading from the sample reading can be performed by the testing apparatus or by the computing device, and either or both of the testing apparatus and the computing device can store the data after the dark reading has been subtracted.

At stage 1955, the computing device can plot data for visualization. For example, the application that executes on the computing device can include instructions to cause a processor of the computing device to generate graphical information corresponding to any of the data captured in stages 1940, 1945, or 1950, including the dark reading, the reference reading (with or without the dark reading subtracted), or the sample reading (with or without the dark reading subtracted). At stage 1960, the computing device can perform a variety of calculations based on the sample reading and the reference reading. For example, the calculations can include a comparison of the sample reading to the reference reading. Such a comparison can help to determine whether a characteristic of the sample fluid under test is sufficiently similar to a corresponding characteristic of the reference sample fluid, for example to ensure a degree of uniformity across different batches of fluid. At stage 1965, the results of the calculations performed in stage 1960 can be output and saved, for example, in a memory element of the computing device.

At stage 1970, the computing device can determine whether more samples should be captured. For example, the application that executes on the computing device can include an interface to allow a user to select whether additional samples should be captured. If no additional samples are to be captured, the process 1900 exits. If additional samples are to be captured, the process 1900 determines at stage 1975 whether the type of sample to be captured next is the same as the type of sample captured previously in stage 1950. If so, the process 1900 returns to stage 1950, in which a new sample reading is captured, and the dark reading is subtracted from the new sample reading. However, if the new sample to be captured is of a different type than the previous sample, the process 1900 instead returns to stage 1945, in which a reference reading is captured. For example, because the sample type has changed, it may be useful to capture a new reference reading corresponding to the new sample type. The process 1900 then proceeds to stage 1950, in which a new sample reading is captured, as described above.

Figure 20:
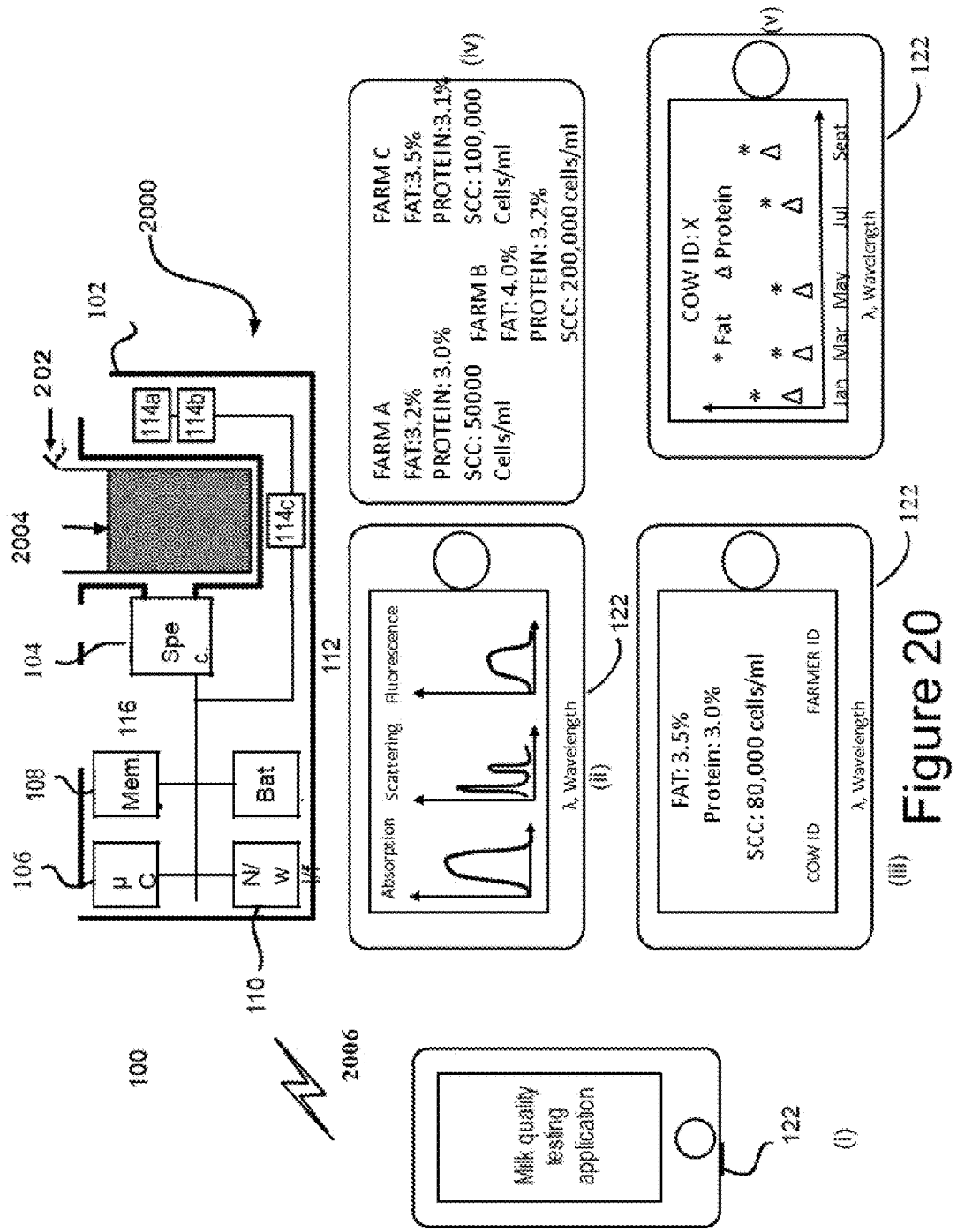
FIG. 20 shows a testing system for measurement of various milk quality parameters using a testing apparatus similar to that shown in FIG. 1.
Figure 21:
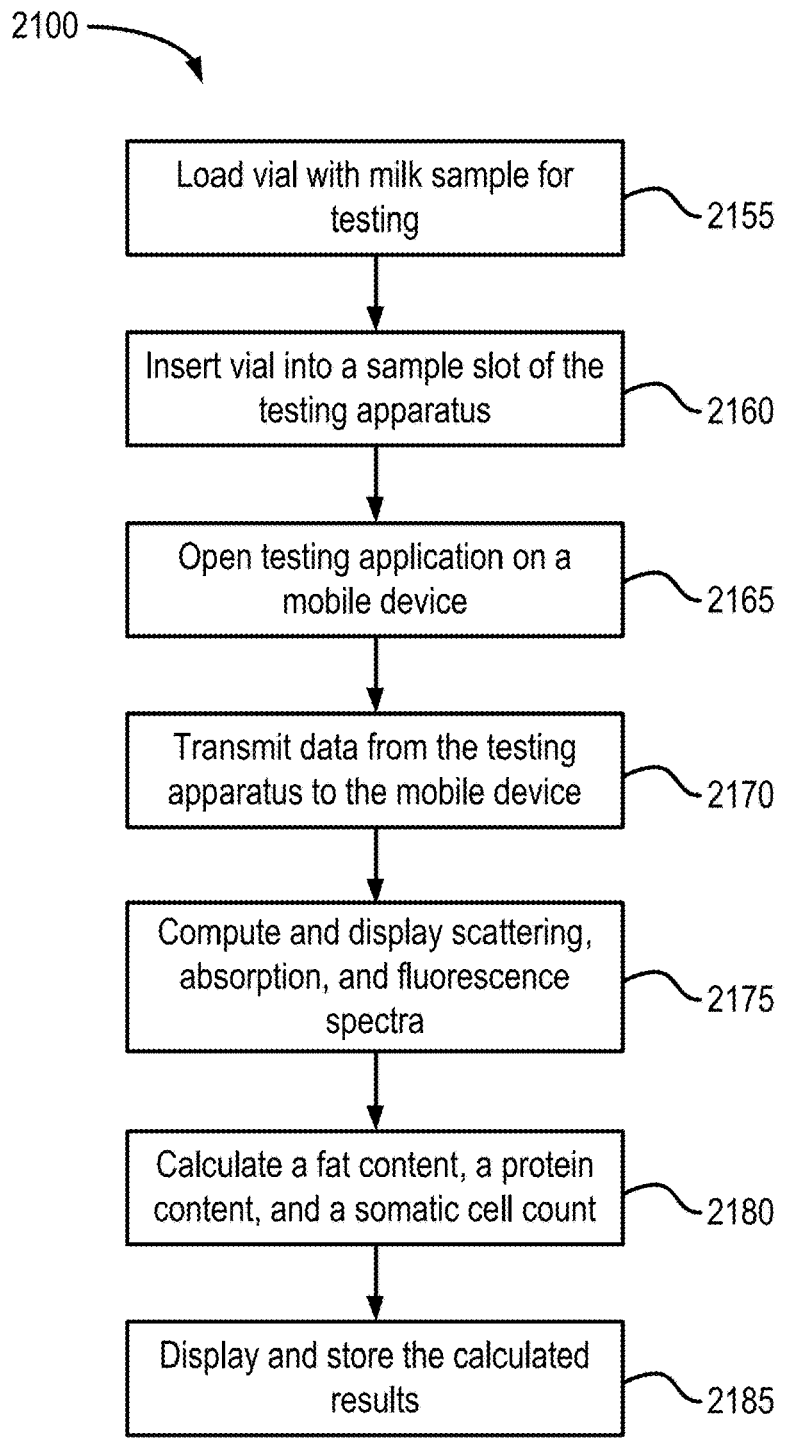
FIG. 21 shows a flow diagram representing an example process of measuring various milk quality parameters using the system of FIG. 20.

FIG. 20 shows a testing system for measurement of various milk quality parameters using a testing apparatus similar to that shown in FIG. 1. FIG. 21 shows a flow diagram representing an example process 2100 of measuring various milk quality parameters using the system of FIG. 20. FIG. 20 also shows example representations of status of a mobile device 122 corresponding to one or more stages of the process 2100. The milk quality parameters can include measurements of fat, protein, and somatic cell counts of a milk sample. The measurements can be taken using the system 2000 of FIG. 20 at a farm or milk collection center. The quality of milk can be measured using these three parameters (i.e., fat percentage, protein percentage, and somatic cell count). Somatic cell count can be expressed, for example, as a number of cells in a unit volume, such as a milliliter, of the milk sample. Farmers are sometimes paid for their milk on the basis of these parameters, and these parameters also can be useful for dairy processors who are involved in the production of milk-based products, such as cheese and yogurt.

Accurately assessing these three parameters on a regular basis can help farmers keep track of a cow's health and take proactive measures if an abnormality is detected. For example, somatic cell counts above a threshold may indicate the onset of infections such as mastitis. If not detected early, the disease can spread to other cows as they use the same milking stations. Beyond a higher threshold, the animal may be culled, which can lead to a significant loss to the farmer. Fat and protein content are also indicators of milk quality and measuring their ratio during early lactation can have predictive value on the cow's performance and health. The proposed device can measure fat percentage using a combination of light scattering in the visible wavelength range (300-800 nm) and regression approaches. For example, protein content can be measured using UV light absorption at 280 nm. Scattering of white light can be used to measure fat content. Somatic cell count can be measured using light-induced fluorescence, in which somatic cells emit green light at around 550 nm when excited by a blue light source at 405 nm. In order to facilitate these measurements, the system 2000 includes a testing apparatus 100 having three separate light sources labeled 114a, 114b, and 114c in FIG. 20. The light sources 114a-114c can be implemented using LEDs or any other form of light source. The light source 114a can be a UV light source to be used for the measurement of protein content of a milk sample 2004 that is loaded into a vial 202 and inserted into the testing apparatus 100. The light source 114b can be a white light source to be used for the measurement of fat content. The light source 114c can be a blue light source to be used for measuring a somatic cell count of the milk sample 2004.

The UV light source 114a and the white light source 114b are positioned opposite the spectrometer 104, and therefore emit light directly through the milk sample 2004 and towards the spectrometer 104. In contrast, the blue light source 114c is positioned such that it directs light at an angle of about 90 degrees with respect to the spectrometer 104. In some implementations, the blue light source 114c can be positioned to direct light at an angle in the range of about 60 degrees to about 120 degrees with respect to the spectrometer 104. This angular offset can be useful because the fluorescence of the somatic cells caused by the blue light source 114c may emitted at a much lower energy than that of the blue light from the blue light source 114c itself. As a result, positioning the blue light source 114c opposite the spectrometer, similar to the positioning of the UV light source 114a and the white light source 114b can cause the signal received by the spectrometer to be overwhelmed by the blue light itself, thereby making it difficult to determine the fluorescence generated by the somatic cells. When the blue light source 114c is positioned at an angle with respect to the spectrometer 104 as shown in FIG. 20A, the blue light itself is not directed towards the spectrometer 104, and therefore the signal received by the spectrometer may more accurately represent the fluorescence produced by somatic cells in the milk sample 2004 in response to the blue light, rather than the blue light itself. In some implementations, the light sources 114a-114c, as well as the sample slot, can be included in a head portion of the testing device, similar to the removable head portion 805 shown in FIGS. 8 and 9.

Referring to FIG. 21, the process 2100 can include receiving, by the testing apparatus, a vial with a milk sample. For example, the process can include loading a vial 202 with a milk sample 2004 for testing (stage 2155) and inserting the vial 202 into a sample slot of the testing apparatus (stage 2160). This is shown in FIG. 20, where the testing apparatus 100 receives a vial 202 containing a milk sample 2004 in the sample slot 118 of the testing apparatus 100. The process 200 further includes receiving an indication from the mobile device that a testing application has been launched (stage 2165). This is shown in FIG. 20(i), where the launching of a milk quality testing application is performed on the mobile device 122. After launching the testing application, the testing application can establish a wireless communication channel 2006 (such as a Bluetooth communication) or a wired communication (such as a USB connection) with the testing apparatus 100. The application can instruct the testing apparatus to proceed with the measurement of the milk sample 2004. To perform the testing, the light sources 114a-114c can be activated, and the spectrometer 104 can be used to record spectral measurements for each light source as described above. In some implementations, the light sources 114a-114c may be activated individually in series. In some implementations, the UV light source 114a and the white light source 114b may be activated simultaneously, and the spectrometer 104 can measure the spectral characteristics of the UV light source 114a and the white light source 114b simultaneously. Then, the light sources 114a and 114b may be deactivated, and the blue light source 114c may be activated to allow the spectrometer to measure spectral characteristics due to the blue light source 114c alone.

The process 2100 further includes transmitting data from the testing apparatus 100 to the mobile device 122 (stage 2170) and computing and displaying absorption, scattering, and fluorescence spectra of the sample (stage 2175). For example, the application executing on the mobile device 122 can measure absorption of the light from the UV light source 114a, scattering of the light from the white light source 114b, and fluorescence of the milk sample 2004 caused by excitation by the light from the blue light source 114c. This is shown in FIG. 20(ii) where the testing application running on the mobile device processes the measurement data received from the testing apparatus 100 and determines the absorption, scattering, and fluorescence spectra of the milk sample. The application displays a graphical representation or visualization of the spectra on an electronic display screen of the mobile device 122. The process 2100 also includes calculating a fat content, a protein content, and a somatic cell count for the milk sample (stage 2180). The application can use stored formulas to determine the protein content based on the calculated absorption of UV light, to determine the fat content based on the calculated scattering of white light, and to determine the somatic cell count based on the calculated fluorescence of the milk sample induced by blue light. The process 2100 further includes the testing application displaying the resulting fat content, protein content, and somatic cell count on a display screen and storing these results as well as batch details in memory (stage 2185). This is shown in FIG. 20(iii). In some implementations, the application can also receive additional information, such as identifier information for the cow who produced the milk sample 2004, the farmer who is performing the testing, or the farm on which the testing was conducted. For example, some such information can be received by the mobile device via one or more RFID tags on the farm or on the cow. The testing application can also integrate with a supply chain tracking database, as shown in FIG. 20(iv), to store or update average milk quality parameters for specific farms, specific cows, or specific farmers. Such information can be used to perform longitudinal milk quality tracking, including by providing information relating to milk quality parameters for a particular cow over time, as shown in FIG. 20(v). The information displayed in FIGS. 20(iv) and 20(v) can be used, for example, by farmers or dairy processors who purchase milk from a variety of farms, in order to determine milk quality on a per-farm or per-cow basis.

Figure 22:
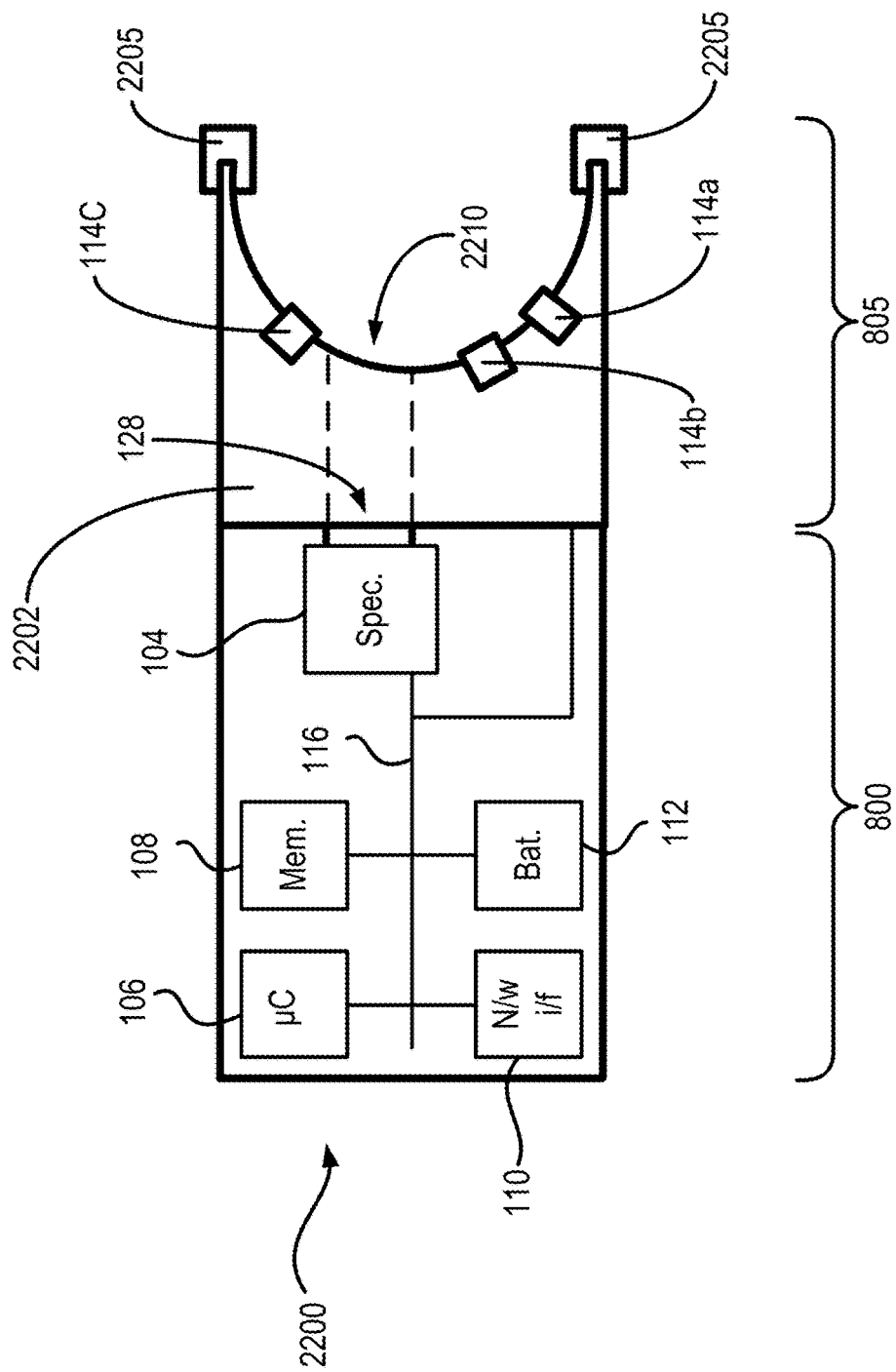
FIG. 22 shows a block diagram of an example testing apparatus.
Figure 24:
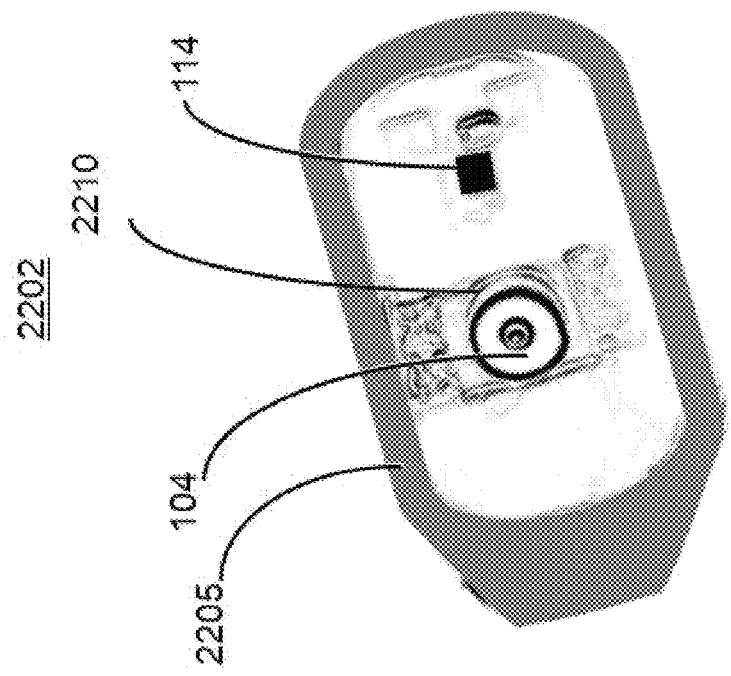
FIG. 24 shows a perspective view of an implementation of the testing apparatus of FIG. 22.
Figure 23:
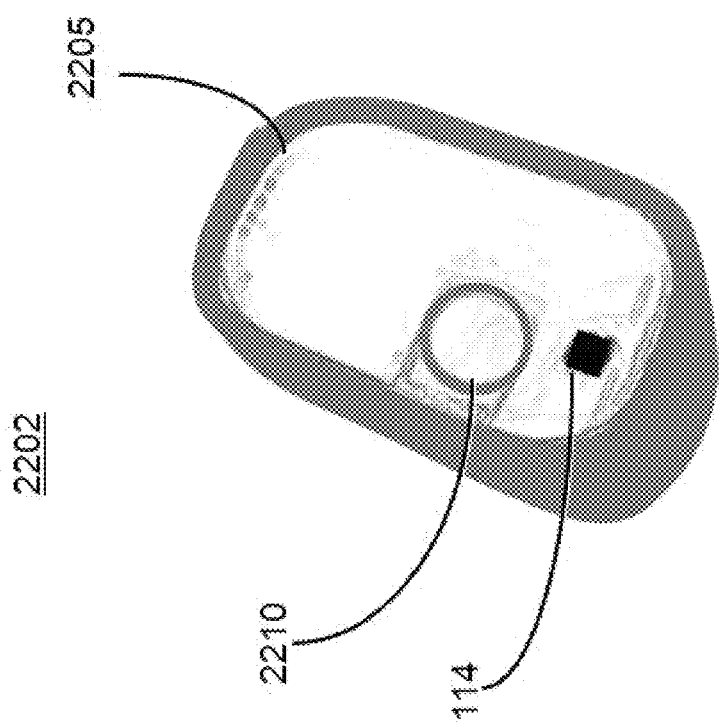
FIG. 23 shows a perspective view of an implementation of the testing apparatus of FIG. 22.

FIG. 22 shows a block diagram of an example testing apparatus 2200. FIG. 23 shows a perspective view of an implementation of the testing apparatus 2200 of FIG. 22. FIG. 24 shows a perspective view of an implementation of the testing apparatus 2200 of FIG. 22. FIGS. 22-24 are described together below. The testing apparatus 100 is similar to the testing apparatus shown in FIGS. 1, 8, and 9, and like reference numerals in the figures refer to like elements. For example, the testing apparatus 2200 includes a body portion 800 and an head portion 805. The head portion 805 can be removably attached to the body portion 800. The head portion 805 includes a reflectance probe 2202. The reflectance probe 2202 is a concave component, and can include light sources 114a, 114b, and 114c. A spacer 2205 is positioned around an edge of the reflectance probe 2202.

The reflectance probe 2202 can be used to measure reflectance of a sample. For example, the sample can be a solid surface or a surface of a liquid. To measure the reflectance of the sample, the testing apparatus 2200 can be positioned such that the spacer 2205 is in contact with a surface of the sample. One or more of the light sources 114a-114c can be activated to direct light towards the surface of the sample, causing the surface of the sample to reflect at least a portion of the light back towards the spectrometer 104. The reflectance probe 2202 includes an opening 2210 aligned with the opening 128 of the body portion 800, which can allow the reflected light to be incident on the spectrometer 104. The spectrometer 104 can therefore measure spectral characteristics of the reflected light.

The light sources 114a-114c can each include a light source configured to emit light having any wavelength or range of wavelengths. For example, the light sources 114a-114c can each be configured to emit red light, blue light, white light, UV light, or any other color or spectrum of light. The light sources 114a-114c may be configured to emit the same or different wavelengths of light relative to one another. In some implementations, the testing apparatus 2200 can include more or fewer light sources than are illustrated in FIG. 22. The light sources 114a-114c can be implemented, for example, as LEDs. The reflectance probe 2202 can also include pass-through electrical connections coupling the light sources 114a-114c to the bus 116, for example to allow the LEDs to receive power and control signals from the components of the body portion 800.

The testing apparatus 2200 can be used, for example, to measure a degree of uniformity between samples. For example, a reflectance of a first sample can be captured using the testing apparatus 2200, and can be compared to a second sample captured using the testing apparatus 2200. In some implementations, spectral data for both samples can be transmitted to a computing device, for example via the network interface 110, and the computing device can be configured to perform a comparison of the spectral data for the two samples in order to determine a degree of uniformity. For example, the samples may be surfaces coated with different batches of paint that are intended to be the same color. The testing apparatus 2200 can therefore be used to help quantify how close in color the two batches of paint are to one another. In some other implementations, the testing apparatus 2200 can be used to detect a marker, such as fluorescence. For example, a sample may include particles or ingredients that produce fluorescence when exposed to light emitted by the light sources 114a-114c. The testing apparatus 2200 can activate the light sources 114a-114c to direct light at the fluid, and the spectrometer 104 can be configured to measure the spectral response of the sample, which can be analyzed (e.g., by a remote computing device) to determine whether the spectral response indicates a presence, or a particular concentration level, of a fluorescent particle or ingredient.

The spacer 2205 can be configured to help ensure uniform conditions across different measurements taken by the testing apparatus 2200. For example, a spectral response can be effected by a distance of the light sources 114a-114c to the sample. The spacer 2205 can be configured to contact a surface of the sample for each measurement in order to ensure that this distance is uniform across different measurements. In some implementations, the spacer 2205 can be removable from the reflectance probe 2202. For example, the spacer 2205 can be configured to be used for one measurement, or a limited number of measurements, before being disposed of and replaced with a new spacer 2205. Such an implementation can be useful in instances in which the sample to be tested may include a substance that could be harmful to the testing apparatus 2200 or to a human operator, such as toxic substance.

FIG. 23 shows a perspective view of the reflectance probe 2202 removed from the body portion 800. As shown, the reflectance probe 2202 of FIG. 23 includes only a single light source 114, rather than three light sources 114a-114c as depicted in FIG. 22. The spacer 2205 is formed by a rim of the reflectance probe 2202. FIG. 24 shows the reflectance probe 2202 attached to the body portion 800. As a result, the spectrometer 104 is visible through the opening 2210.

While operations are depicted in the drawings in a particular order, such operations are not required to be performed in the particular order shown or in sequential order, and all illustrated operations are not required to be performed. Actions described herein can be performed in a different order.

Having now described some illustrative implementations, it is apparent that the foregoing is illustrative and not limiting, having been presented by way of example. Features that are described herein in the context of separate implementations can also be implemented in combination in a single embodiment or implementation. Features that are described in the context of a single implementation can also be implemented in multiple implementations separately or in various sub-combinations. References to implementations or elements or acts of the systems and methods herein referred to in the singular may also embrace implementations including a plurality of these elements, and any references in plural to any implementation or element or act herein may also embrace implementations including only a single element. References in the singular or plural form are not intended to limit the presently disclosed systems or methods, their components, acts, or elements to single or plural configurations. References to any act or element being based on any act or element may include implementations where the act or element is based at least in part on any act or element.

The phraseology and terminology used herein is for the purpose of description and should not be regarded as limiting. The use of "including" "comprising" "having" "containing" "involving" "characterized by" "characterized in that" and variations thereof herein, is meant to encompass the items listed thereafter, equivalents thereof, and additional items, as well as alternate implementations consisting of the items listed thereafter exclusively. In one implementation, the systems and methods described herein consist of one, each combination of more than one, or all of the described elements, acts, or components.

Any implementation disclosed herein may be combined with any other implementation or embodiment, and references to "an implementation," "some implementations," "one implementation" or the like are not necessarily mutually exclusive and are intended to indicate that a particular feature, structure, or characteristic described in connection with the implementation may be included in at least one implementation or embodiment. Such terms as used herein are not necessarily all referring to the same implementation. Any implementation may be combined with any other implementation, inclusively or exclusively, in any manner consistent with the aspects and implementations disclosed herein.

References to "or" may be construed as inclusive so that any terms described using "or" may indicate any of a single, more than one, and all of the described terms. References to at least one of a conjunctive list of terms may be construed as an inclusive OR to indicate any of a single, more than one, and all of the described terms. For example, a reference to "at least one of 'A' and 'B'" can include only 'A', only 'B', as well as both 'A' and 'B'. Such references used in conjunction with "comprising" or other open terminology can include additional items.

Where technical features in the drawings, detailed description or any claim are followed by reference signs, the reference signs have been included for the sole purpose of increasing the intelligibility of the drawings, detailed description, and claims. Accordingly, neither the reference signs nor their absence have any limiting effect on the scope of any claim elements.

Modifications of described elements and acts such as variations in sizes, dimensions, structures, shapes and proportions of the various elements, values of parameters, mounting arrangements, use of materials, colors, orientations can occur without materially departing from the teachings and advantages of the subject matter disclosed herein. For example, elements shown as integrally formed can be constructed of multiple parts or elements, the position of elements can be reversed or otherwise varied, and the nature or number of discrete elements or positions can be altered or varied. Other substitutions, modifications, changes and omissions can also be made in the design, operating conditions and arrangement of the disclosed elements and operations without departing from the scope of the present disclosure.

The systems and methods described herein may be embodied in other specific forms without departing from the characteristics thereof. For example, descriptions of positive and negative electrical characteristics may be reversed. For example, elements described as negative elements can instead be configured as positive elements and elements described as positive elements can instead by configured as negative elements. Further relative parallel, perpendicular, vertical or other positioning or orientation descriptions include variations within +/−10% or +/−10 degrees of pure vertical, parallel or perpendicular positioning. References to "approximately," "substantially" or other terms of degree include variations of +/−10% from the given measurement, unit, or range unless explicitly indicated otherwise. Coupled elements can be electrically, mechanically, or physically coupled with one another directly or with intervening elements. Scope of the systems and methods described herein is thus indicated by the appended claims, rather than the foregoing description, and changes that come within the meaning and range of equivalency of the claims are embraced therein.

What is claimed is:

1. A system of testing fluid samples, comprising:
   a portable testing apparatus having a head portion and a body portion, the portable testing apparatus comprising:
   the head portion having a length of between 2 centimeters and 3 centimeters, a width of between 3 centimeters and 4 centimeters, and a height of between 2 centimeters and 4 centimeters, the head portion including a sample aperture to receive a fluid sample and a light source to direct light towards the fluid sample; and
   the body portion coupled with the head portion, the body portion having a length of between 5 centimeters and 10 centimeters, a width of between 4 centimeters and 7 centimeters, and a height equal to the height of the head portion, the body portion including a microcontroller, a memory, a battery, a network interface, and a spectrometer, the spectrometer aligned with the light source of the head portion to receive the light from the light source after the light has passed through the fluid sample to produce spectral data;
   a capillary attachment to be inserted through the sample aperture of the head portion of the portable testing apparatus and into a slot included in the head portion of the portable testing apparatus, the capillary attachment comprising an opening having a diameter of between 1 millimeter and 1.5 millimeters;
   a capillary tube to be inserted through the opening of the capillary attachment, the capillary tube to receive the fluid sample and transport the fluid sample into the head portion of the portable testing apparatus; and
   a computing device communicatively coupled to the portable testing apparatus via the network interface of the portable testing apparatus to receive the spectral data from the portable testing apparatus, the computing device including an electronic processor that executes an application to process the spectral data to generate a measurement value of the fluid sample.

2. The system of claim 1, comprising:
   a glass slide to receive the fluid sample, wherein the sample aperture of the head portion includes a rectangular opening, the glass slide having a width larger than a width of the rectangular opening, the sample aperture comprising a slot extending outward from opposing edges of the rectangular opening to receive the glass slide.

3. The system of claim 2, comprising:
   the glass slide having a length of between 20 millimeters and 30 millimeters, a width of between 20 millimeters and 30 millimeters, and a thickness of between 0.15 millimeters and 1.2 millimeters; and
   the slot having a width equal to the width of the glass slide.

4. The system of claim 1, comprising:
the aperture extending laterally through an entirety of the head portion of the portable testing apparatus along a direction parallel to the height of the head portion, the aperture to receive a feed tube containing the sample fluid.

5. The system of claim 1, comprising:
a feed tube to receive the sample fluid from a pipe that transports the fluid.

6. The system of claim 5, comprising:
the feed tube to receive a portion of the fluid transported by the pipe, wherein the feed tube transports fluid in parallel with the pipe.

7. The system of claim 5, comprising:
the feed tube to receive a portion of the fluid transported by the pipe, wherein the feed tube transports fluid in series with the pipe.

8. The system of claim 1, comprising:
the network interface including a Bluetooth interface.

9. The system of claim 1, comprising:
the microcontroller to control operation of the memory, the network interface, and the spectrometer.

10. The system of claim 1, comprising:
the memory element to store at least a portion of the spectral data.

11. The system of claim 1, comprising:
the computing device including an electronic display, wherein execution of the application to process the spectral data to generate the measurement value of the fluid sample causes the electronic display to show a visualization of the measurement value.

12. The system of claim 1, comprising:
the head portion to be removably attached to the head portion of the portable testing apparatus.

13. The system of claim 1, wherein:
the sample fluid comprises one of beer or wine.

14. The system of claim 1, comprising:
a second light source positioned within the head portion of the portable testing apparatus, the second light source oriented to direct light toward the fluid sample at an angle between 60 degrees and 120 degrees with respect to an input of the spectrometer.

15. A method of testing fluid samples, comprising:
receiving, in a sample aperture of a head portion of a portable testing apparatus, a fluid sample, the head portion having a length of between 2 centimeters and 3 centimeters, a width of between 3 centimeters and 4 centimeters, and a height of between 2 centimeters and 4 centimeters, wherein a capillary attachment is inserted through the sample aperture of the head portion of the portable testing apparatus and into a slot included in the head portion of the portable testing apparatus, the capillary attachment comprising an opening having a diameter of between 1 millimeter and 1.5 millimeters, and wherein a capillary tube is inserted through the opening of the capillary attachment, the capillary tube to receive the fluid sample and transport the fluid sample into the head portion of the portable testing apparatus;
activating a light source included in the head portion of the portable testing apparatus to direct light toward the fluid sample;
receiving, by a spectrometer included in a body portion of the portable testing apparatus, the light from the light source after the light has passed through the fluid sample;
producing, by the spectrometer, spectral data based on the light received from the light source;
transmitting, via network interface included in the body portion of the portable testing apparatus, the spectral data to a computing device; and
executing, by the computing device, an application to process the spectral data to generate a measurement value of the fluid sample.

16. The method of claim 15, comprising:
calibrating the portable testing apparatus before receiving the sample fluid.

17. The method of claim 15, comprising:
comparing, by the computing device, the measurement value to a reference measurement value.

18. The method of claim 15, comprising:
receiving, in the sample aperture of the head portion of the portable testing apparatus, the capillary attachment and the capillary tube, wherein the sample fluid is delivered to the head portion of the portable testing apparatus via the capillary tube.

19. The method of claim 15, wherein:
receiving the sample fluid comprises receiving one of beer or wine.

20. The method of claim 15, wherein:
the measurement value relates to at least one of a standard reference method number, a wort color, an international bitterness unit, a tone, or an intensity.

* * * * *